United States Patent [19]
Larsen et al.

[11] Patent Number: 5,523,318
[45] Date of Patent: Jun. 4, 1996

[54] PYRROLIDINO-SUBSTITUTED OXIMES USEFUL AS ANTI-ATHEROSCLEROSIS AND ANTI-HYPERCHOLESTEROLEMIC AGENTS

[75] Inventors: Scott D. Larsen; Charles H. Spilman, both of Kalamazoo, Mich.

[73] Assignee: The Upjohn Company, Kalamazoo, Mich.

[21] Appl. No.: 466,181

[22] Filed: Jun. 6, 1995

Related U.S. Application Data

[60] Division of Ser. No. 313,684, filed as PCT/US93/04059, May 5, 1993, which is a continuation-in-part of Ser. No. 900,229, Jun. 17, 1992, abandoned.

[51] Int. Cl.$^6$ .................. A61K 31/415; C07D 231/54
[52] U.S. Cl. .................. 514/406; 548/110; 548/360.1
[58] Field of Search .................. 514/406; 548/373, 548/374, 378

[56] References Cited

FOREIGN PATENT DOCUMENTS 0299209  6/1988  European Pat. Off. .

Primary Examiner—Marianne M. Cintins
Assistant Examiner—Phyllis G. Spivack
Attorney, Agent, or Firm—Donald L. Corneglio

[57] ABSTRACT

Pyrrolidinopyrazole-substituted oximes having the formula

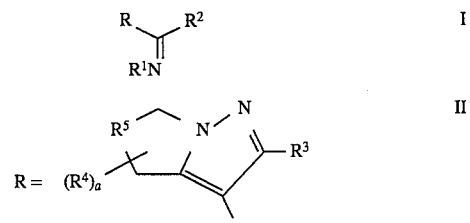

are disclosed wherein $R^1$, $R^2$, $R^3$, $R^4$, $R^5$ and a are as described in the claims for the treatment of atherosclerosis and hypercholesterolemia.

4 Claims, No Drawings

PYRROLIDINO-SUBSTITUTED OXIMES USEFUL AS ANTI-ATHEROSCLEROSIS AND ANTI-HYPERCHOLESTEROLEMIC AGENTS

CROSS-REFERENCE TO RELATED APPLICATIONS

This application is a divisional of U.S. Ser. No. 08/313,684, filed September 1994, now pending, which is a continuation-in-part of International Application No. PCT/US93/04059, filed 5 May 1993, which was a continuation-in-part of U.S. Ser. No. 07/900,229 filed 17 Jun. 1992, now abandoned.

FIELD OF INVENTION

The present invention relates to imidazopyridino-, pyrazolopyridino-, pyrazolapyrrolidino- and pyrozoloazepino-substituted oximes, useful for the treatment of atherosclerosis and hypercholesterolemia.

BACKGROUND OF THE INVENTION

Atherosclerosis is a major cause of morbidity and mortality in the United States and Western European countries. Hypercholesterolemia, especially increased levels of low density lipoprotein (LDL) cholesterol, has been shown to be related to an increased risk of coronary heart disease (CHD) (Lowering blood cholesterol to prevent heart disease: NIH consensus development conference statement. (1985) Arteriosclerosis 5: 404–412). In the United States alone, hypercholesterolemia contributes to 1.5 million myocardial infarctions per year and up to 0.5 million people die as a direct result of atherosclerotic cardiovascular disease (Lipid Research Clinics Program. The Lipid Research Clinics primary prevention trial results: the relationship of reduction in incidence of coronary heart disease to cholesterol lowering. (1984) JAMA 251: 365–374). It is estimated that as many as 40 million people in the United States between the ages of 40 to 70 years have high cholesterol levels and are candidates for lipid-lowering therapy. The National Cholesterol Education Program (NCEP), sponsored by the National Heart, Lung and Blood Institute, is a major national effort to educate physicians and the public about the risks associated with high blood cholesterol levels. In addition, the NCEP has suggested guidelines to identify and treat patients with high serum cholesterol (Report of the National Cholesterol Education Program Expert Panel on Detection, Evaluation, and Treatment of High Blood Cholesterol in Adults. (1988) Arch. Intern. Med. 148: 36–69).

There is substantial evidence that lowering total and LDL cholesterol reduce the risk of CHD. Of particular interest are the outcomes of several angiographic trials of decreased total and LDL cholesterol (Blankenhorn, D. H., Nessim, S. A., Johnson, R. L. et al. (1987) Beneficial effects of combined colestipol-niacin therapy on coronary atherosclerosis and coronary venous bypass grafts. JAMA 257: 3233–3240. Brensike, J. F., Levy, R. I., Kelsey, S. F. et al. (1984) Effects of therapy with cholestyramine on progression of coronary arteriosclerosis: results of the NHLBI Type II Coronary Intervention Study. Circulation 69: 313–324. Brown, G., Albers, J. J., Fisher, L. D. et al. (1990) Regression of coronary artery disease as a result of intensive lipid-lowering therapy in men with high levels of apolipoprotein B. N. Engl. J. Med. 323:1289–1298. Buchwald. H., Varco, R. L., Matts, J. P. et al. (1990) Effect of partial ileal bypass surgery on mortality and morbidity from coronary heart disease in patients with hypercholesterolemia: report of the Program on the Surgical Control of the Hyperlipidemias (POSCH). N. Engl. J. Meal. 323: 946–955. Cashin-Hemphill, L., Mack, W. J., Pogoda, J. et al. (1990) Beneficial effects of colestipol-niacin on coronary atherosclerosis: a 4-year follow-up. JAMA 264: 3013–3017. Kane, J. P., Malloy, M. J., Ports, T. A. et al. (1990) Regression of coronary atherosclerosis during treatment of familial hypercholesterolemia with combined drug regimens. JAMA 264: 3007–3012. Ornish, D., Brown, S. E., Sherwitz, L. W. et al. (1990) Can lifestyle changes reverse coronary heart disease? The Lifestyle Heart Trial. Lancet 336:129–133.). These studies in patients with high, average or low baseline cholesterol levels achieved cholesterol reductions with drugs, partial ileal bypass or diet. These studies provided evidence that cholesterol reduction can slow the progression of atherosclerotic lesions, and actually induce regression of existing lesions. Therefore, there is convincing evidence that lowering total and LDL cholesterol is beneficial (Rifkind, B. M. and Grouse, L. D. (1990) Cholesterol redux. JAMA 264: 3060–3061. LaRosa, J. C. and Cleeman, J. I. (1992) Cholesterol lowering as a treatment for established coronary heart disease. Circulation 85: 1229–1235) not only in terms of primary prevention of CHD but also in secondary prevention.

INFORMATION DISCLOSURE

European Patent Application 0 299 209 discloses oxime-substituted derivative of pyrazolopyridino for use as intermediates (see, Example 4, page 23) and pyrazolo(1,5-a)pyridine derivatives for use as cardiotonic agents (Formula 1a, page 4). These compounds are excluded by proviso in this invention but the use or method of treating atherosclerosis or hypercholesterolemia is not suggested or disclosed.

SUMMARY OF INVENTION

A compound having the formula

I wherein R is selected from the group consisting of

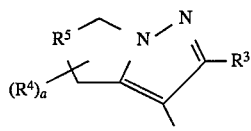

II

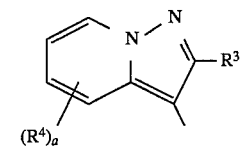

III

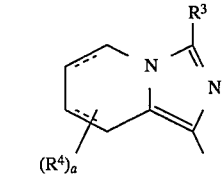

IV

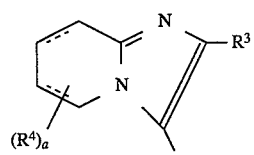

V $R_1$ is
(a) hydroxy,
(b) $OC(O)C_1$-$C_5$ alkyl,
(c) O—$C_1$-$C_5$ alkyl —OH, and
(d) $NHC(O)C_1$-$C_5$ alkyl; or $R_2$ is
(a) straight chain $C_1$-$C_8$ alkyl, or
(b) phenyl-X,
(c) $C_1$-$C_5$ alkyl-$R^6$-phenyl-X;

$R_3$ is
(a) hydrogen,
(b) $C_1$-$C_8$ alkyl,
(c) furanyl,
(d) $C_1$-$C_5$ alkyl-$R^6$-phenyl-X,
(e) phenyl-X, or
(f) Si $(C_1$-$C_5$ alkyl$)_3$;

$R_4$ is
(a) phenyl-X,
(b) $C_1$-$C_5$ alkyl-phenyl-X,
(c) halogen,
(d) $C_1$-$C_8$ alkyl,
(e) OH,
(f) $OC_1$-$C_5$ alkyl-phenyl-X,
(g) $NHC(O)C_1$-$C_5$ alkyl,
(h) $OC(O)C_1$-$C_5$ alkyl;
(i) hydrogen, or
(j) $R_4$ can be —$(CH_2)_b$— or $(CH)_4$— which together with two adjacent carbons on the ring to which it is attached form an additional ring;

$R^5$ is —$(CH_2)_c$—;
$R^6$ is,
(a) O—,
(b) S—, or
(c) —$CH_2$—;

a is 0–4;
b is 3–6;
c is 1-14 6;

phenyl-X is phenyl substituted by 1 to 3 of the same or different substituent selected from the group
(a) H,
(b) halogen,
(c) OH,
(d) $OC_1$-$C_5$ alkyl,
(e) $SC_1$-$C_5$ alkyl,
(f) $NH_2$,
(g) $N(C_1$-$C_5$ alkyl$)_2$,
(h) $NHC(O)C_1$-$C_5$ alkyl,
(i) $OC(O)C_1$-$C_5$ alkyl,
(j) $CF_3$,
(k) CN, or
(l) $CO_2$ $C_1$-$C_5$ alkyl;

pharmaceutically acceptable acid addition salts thereof; with proviso that the compound cannot be Ethanone, 1-(4,5,6,7-tetrahydropyrazolo[1,5-a]pyridin-3-yl)- , oxime;

Ethanone, 1-[4,5,6,7-tetrahydro-2-[(phenylthio)methyl]pyrazolo[1,5-a]pyridin-3-yl]—, oxime;

Ethanone, 1-(2-methylpyrazolo[1,5-a]quinolin-3-yl)-, oxime; or

Ethanone, 1-imidazo[1,2-a]pyridin-3-yl-, oxime when defining the treatment of atherosclerosis or hypercholesterolemia but with the further proviso where $R_1$ is hydroxy or —$NHC(O)C_1$-$C_5$)alkyl, $R_2$ is not $C_1$-$C_6$ alkyl, $R_3$ is not $C_1$-$C_6$ alkyl or phenyl-X and $R_4$ is not halogen, $C_1$-$C_6$ alkyl or hydrogen when defining compounds of this invention.

The compounds of this invention may be supplied in capsules, tablets, suppositories, powders, or as fluid solutions and/or suspensions in aqueous or non-aqueous vehicles or can be added to food. The compounds can be administered orally, intravenously, intramuscularly, intra-arterially, intraperitoneally, subcutaneously, sublingually, bucally to man or to other animals. The dosage of each of the uses is about 0.1–200 mg/kg. The dosage will vary with the route of administration and the physical state of the recipient. Also, for example, the dosage by the oral route will depend on the frequency of administration and the weight of the recipient.

Without further elaboration, it is believed that one skilled in the art can, using the preceding description, practice the present invention to its fullest extent. The following detailed examples describe how to prepare various compounds of the invention and are to be construed as merely illustrative, and not limitations of the preceding disclosure. Those skilled in the art will promptly recognize appropriate variations from the procedures both as to reactants and as to reaction conditions and techniques.

The carbon atom content of various hydrocarbon-containing moieties is indicated by a prefix designating the minimum and maximum number of carbon atoms in the moiety, i.e., the prefix $(C_i$-$C_j)$ indicates a moiety of the integer "i" to the integer "j" carbon atoms, inclusive. Thus $(C_1$-$C_8)$alkyl refers to alkyl of one to eight carbon atoms, inclusive, or methyl, ethyl, propyl, butyl, and isomeric forms thereof.

Examples of phenyl-X include phenyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4- 2,3,6-, or 2,4,5-)trimethylphenyl, (o-, m-, or p-)fluorophenyl, (o-, m-, or p-trifluoromethyl)phenyl, 4-fluoro-2,5-xylyl, (2,4-, 2,5-, 2,6-, 3,4, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-)trifluoro-methylphenyl, (o-, m-, or p-)ethoxyphenyl, (4- or 5-)chloro-2 -methoxy-phenyl, and 2,4-dichloro-(5- or 6-)methylphenyl, and the like.

Halogen is fluoro, chloro, bromo, or iodo or trifluoromethyl.

It will be apparent to those skilled in the art that the oximes of this invention or their derivative may be syn or anti or mixtures thereof. The scope of this invention includes all enantiomeric or diastereomeric forms of Formula I compounds either in pure form or as mixtures of enantiomers or diastereomers. The therapeutic properties of the compounds may to a greater or lesser degree depend on the stereochemistry of a particular compound. Pure enantiomers as well as enantiomeric or diastereomeric mixtures are within the scope of the invention. Examples of pharmaceutically acceptable acid addition salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate.

EMBODIMENTS OF THE INVENTION

The methods of preparing the compounds of the invention are illustrated schematically below.

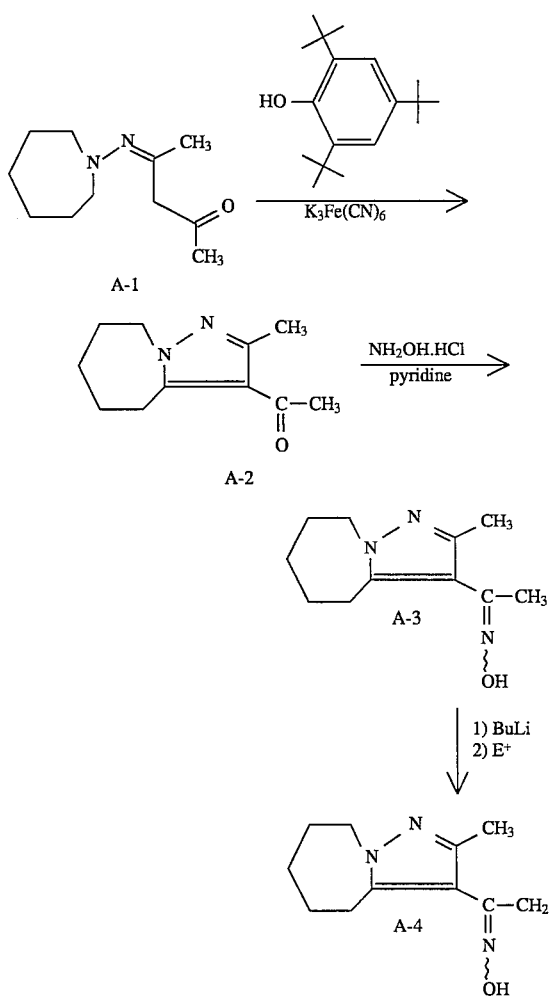

In step 1, A-1 is reacted with 2,4-6-tri-t-butylphenol in the presence of potassium ferricyanide to yield A-2. In step 2, A-2 is reacted with hydroxylamine hydrochloride to yield A-3. In step 3, A-3 is reacted with n-butyl lithium and then with a source of electrophile E$^+$ such as diphenyldisulfide or methyliodide, to yield A-4. This procedure is discussed in Dimroth, K.; Tunscher, W. Synthesis 1977, 339.

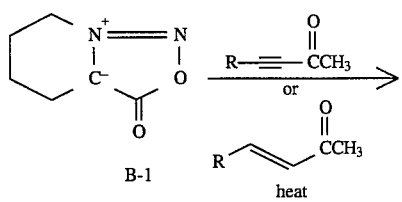

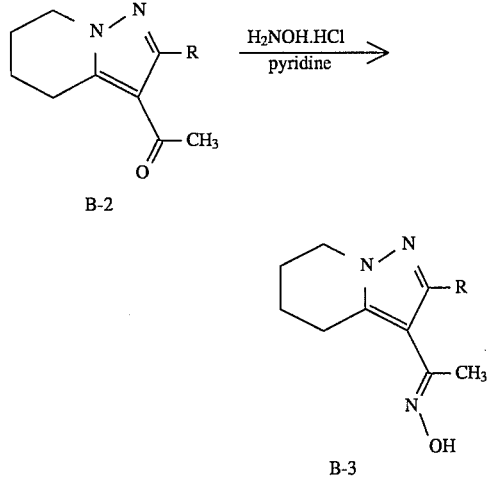

In step 1, B-1 is either reacted with a substituted acetylene or heated with an olefin to yield B-2. In step 2, B-2 is reacted with hydroxylamine hydrochloride to yield B-3. This procedure is based upon the procedure of Ranganathan, D.; Bamezai, S. Syn. Comm. 1985, 15, 259. Huisgen, R.; Grashey, R.; Gotthardt, H.; Schmidt, R. Ang. Chem. Int. Ed. 1962, 1, 48. Huisgen, R.; Gotthardt, H., Grashey, R. Chem. Ber. 1968, 101,536. Hammick, D. L.; Voaden, D. J. J. Chem. Soc. 1961, 3303. Ranganathan, D.; Bamezai, S. Tet. Lett. 1983, 24, 1067.

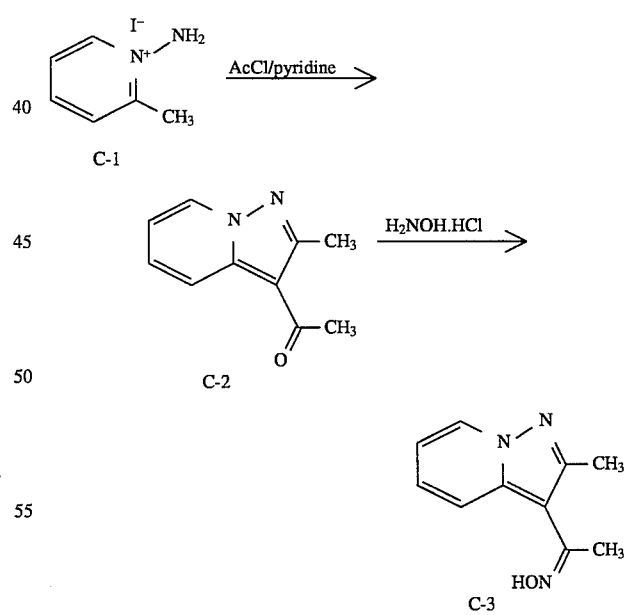

In step 1, C-1 is reacted with acetyl chloride to yield C-2. In step 2, C-2 is reacted with hydroxylamine hydrochloride to yield C-3. This procedure is based upon the procedure of Potts, K. T.; Singh, U. P.; Bhattacharyya, J. J. Org. Chem. 1968, 33, 3766, Potts, K. T.; Dugas, R.; Surapaneni, C. R. J. Het. Chem. 1973, 10, 821.

Scheme D

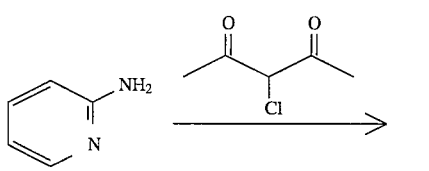

D-1

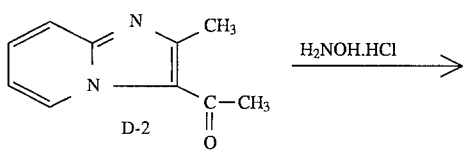

D-2

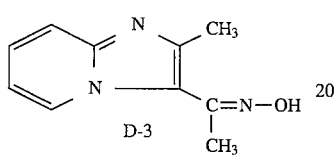

D-3

In step 1, aminopyridine D-1 is reacted with 3-chloro-2,4-pentanedione to form D-2. In step 2, D-2 is reacted with hydroxylamine hydrochloride to form D-3.

Scheme E

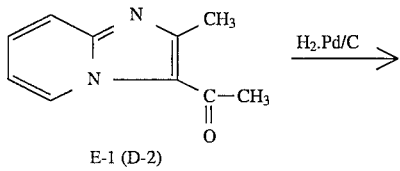

E-1 (D-2)

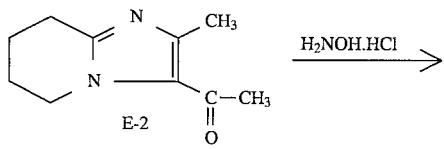

E-2

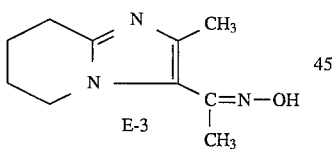

E-3

In step 1, E-1 (D-2) is reduced to form E-2. Step 2 is conducted in the same manner as step 2 of Scheme D to yield E-3. The synthesis of E-1 is based on the procedures of Schilling et al; Chem. Ber., 1955, 88, 1093; and Mosby et al; "Heterocyclic Systems with Bridgehead Nitrogen Atoms Pt. 1"; Interscience; 1961, 462.

Scheme F

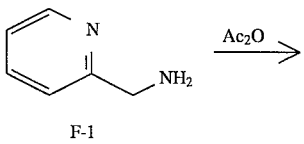

F-1

Scheme F -continued

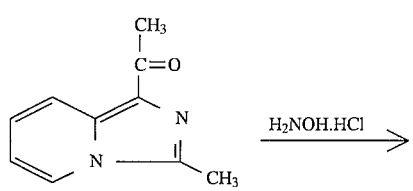

F-2

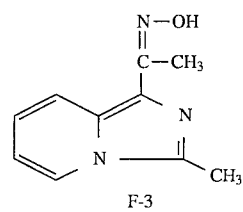

F-3

In step 1, 2-(aminomethyl)pyridine F-1 is reacted with acetic anhydride to yield F-2. In step 2, F-2 is reacted with hydroxylamine hydrochloride to yield F-3. This procedure is based upon the procedure described by Bower et al; J. Chem. Soc., 1955, 2834.

Scheme G

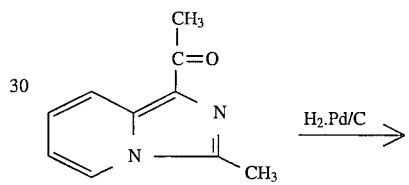

G-1

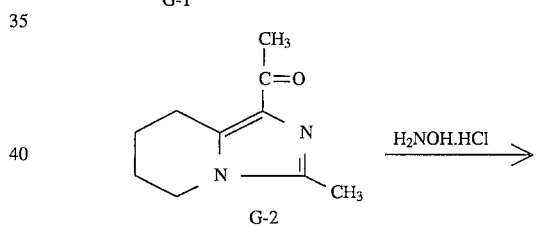

G-2

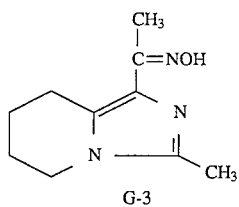

G-3

This scheme is similar to the process of scheme F except that G-1 (F-2) is hydrogenated to yield G-2 and then G-2 reacted with hydroxylamine hydrochloride to yield G-3.

The starting compounds for schemes A to G are either commercially available, can be prepared by methods well known in the art or are described herein.

Compounds of this invention wherein $R^1$ is hydroxy can be converted to compounds wherein $R^1$ is alkyl carboxy or hydroxy alkyloxy by methods well known in the art.

Preparation 1

Ethanone, 1-(5,6,7,8-tetrahydro-2-methyl-4H-pyrazolo[1,5-a]azepine-3-yl), (A-2, Scheme A)

To a stirred mixture of a solution of 30 g (0.75 mole) of sodium hydroxide in 400 mL of water and 164.7 g (0.5 mole)

of potassium ferricyanide under nitrogen was added a solution of 19.6 g (0.1 mole) of 2,4-pentanedione, mono(1-aminotetrahydroazepine)hydrazone and 26.2 g (0.1 mole) of 2,4,6-tri-t-butylphenol in 200 mL of methylene chloride during 12 minutes. During the addition, the temp. rose to 35° C. and the color of the reaction changed from red to dk. green. The mixture was stirred for 23 hrs. The mixture was diluted with water (200 mL) and extracted with methylene chloride (2×200 mL). The extracts were dried over magnesium sulfate and concentrated in vacuo, leaving a yellow-brown semi-solid (45 g). Column chromatography (1.1 kg silica, 20% ethyl acetate/methylene chloride, 200 mL fractions) gave 11.1 g in fractions 27–60. Recrystallization from ether-Skellysolve B provided 9.35 g of the title compound as ivory needles (m.p. 96°–97° C.).

Preparation 2

Ethanone, 1-(4,5,6,7-tetrahydro-2-methylpyrazolo[1,5a]pyridin-3-yl)- (B-2, Scheme 2)

[1,2,3]Oxadiazolo[3.4-a]pyridin-8-ium, 3,3a,4,5,6,7-hexahydro-3-oxo, ylide (3.17 g, 22.6 mmole) and 3-penten-2-one (11.8 mL, 79.1 mmole) were refluxed in toluene (23 mL) for 16 hours. The excess reagents were removed under reduced pressure to afford an amber oil, containing a 6:1 ratio of Ethane, 1-(4,5,6,7-tetrahydro-2-methylpyrazolo[1, 5-a]-pyridin-3-yl)- Ethanone, 1-(4,5,6,7-tetrahydropyrazolo [1,5-a]pyridin-3-yl)- . The two compounds were separated by flash chromatography (60% ethyl acetate/hexane, 300 g silica) to produce 2.62 g (65%) of Ethane, 1-(4,5,6,7 -tetrahydro-2-methylpyrazolo[1.5-a]-pyridin-3-yl)- of as yellow crystals. An analytical sample was prepared by recrystallization from refluxing hexane (m.p. 67°–69° C.).

$^1$H NMR(CDCl$_3$)δ 4.08 (t, 2H, NCH$_2$, J=6 Hz), 3.04 (t, 2H, 4-CH$_2$, J=6 Hz) 2.47 (s, 3H, CH$_3$), 2.41 (s, 3H, CH$_3$), 1.8–2.0 (m, 4H, CH$_2$); IR (mull) 1646, 1534, 1515, 1348, 1134, 1080, 987 cm$^{-1}$; UV (EtOH) $\lambda_{max}$ (ϵ) 250 (13140); MS m/e (relative intensity) 178 (M$^+$, 31), 164 (11), 163 (100), 135 (8), 43 (10); Anal. Calcd for C$_{10}$H$_{14}$N$_2$O: C, 67.39; H, 7.92; N, 15.72; Found: C, 67.52; H, 7.98; N, 15.69; TLC (SiO$_2$) R$_f$=0.27, 60% ethyl acetate/hexane.

Preparation 3

Ethanone, 1-(5,6-dihydro-2-methyl-4H-pyrrolo[1,2-b]pyrazol-3-yl)- (B-2, Scheme B)

4H-Pyrrolo[1,2-c][1,2,3]oxadiazol-7-ium, 5,6-dihydro-3-hydroxy-, hydroxide, inner salt (100 mg, 0.79 mmole) and 3-penten-2-one (0.47 mL, 2.8 mmole) were refluxed in xylene (1 mL) for 18 hours. The excess reagents were removed under reduced pressure to produce a dark brown oil. This oil was purified by flash chromatography (70% ethyl acetate/hexane, 10 g silica) to afford 77.6 mg (60%) of pale yellow crystals. An analytical sample of the title compound was prepared by recrystallization from hexane (m.p. 88°–90° C.).

$^1$H NMR (CDCl$_3$)δ 4.10 (t, 2H, NCH$_2$, J=7.3 Hz), 3.10 (t, 2H, 4-CH$_2$, J=7.2 Hz), 2.5–2.7 (m, 2H, CH$_2$), 2.46 (s, 3H, CH$_3$), 2.33 (s, 3H, CH$_3$); IR (mull) 1667, 1664 1536, 1357, 1110, 1019, 958, 879, 636 cm$^{-1}$; UV (EtOH) $\lambda_{max}$ (ϵ) 245 (13400); MS m/e (relative intensity) 165 (10), 164 (M$^+$, 92), 150 (32), 149 (100), 43 (35); Anal. Calcd for C$_9$H$_{12}$N$_2$O: C, 65.83; H, 7.37; N, 17.06; Found: C, 65.51; H, 7.74; N, 17.11; TLC (SiO$_2$) R$_f$=0.29, 80% ethyl acetate/hexane.

Preparation 4

Ethanone, 1-(2-methylimidazo[1,2-a]pyridin-3-yl) (D-2, Scheme D)

Prepared as in: K. A. Petrov, patent SU 522-187.

Preparation 5

Ethanone, 1-(2,5-dimethylimidazo[1,2-a]pyridin-3-yl) (D-2, Scheme D)

To a solution of 6-methyl-2-aminopyridine (3 g, 28 mmole) in DMF (15 mL) was added dropwise 3-chloro-2,4-pentanedione (3.77 g, 28 mmole). The solution was stirred at 65° C. for 1.5 hrs. Solvent was removed in vacuo. The residue was chromatographed (silica, Skellysolve B, the 1/1 acetone/Skellysolve B) to give an oil which crystallized (1.2 g). The crude material was taken up in chloroform, subjected to Darco, and concentrated. Recrystallization from Skellysolve B (75 mL) gave 0.9 g (m.p. 100°–102° C.).

$^1$H NMR (CDCl$_3$) 7.54 (m, 1H), 7.34 (m, 1H), 6.80 (dd, J=6 Hz), 2.77 (s, 3H), 2.67 (s, 3H), 2.47 (s, 3H); IR (cm$^{-1}$) 1642.

Preparation 6

Ethanone, 1-(3-methyl,5,6,7,8-tetrahydroimidazo[1,5-a]pyridin-1-yl) (G-2, Chart G)

Ethanone, 1-(3-methylimidazo[1,5-a]pyridin-1-yl)- (Bower et al, J. Chem. Soc. 2834 (1955)) (2.0 g, 11.5 mmole) was dissolved in methanol (25 mL) and 10% Pd/C (0.2 g) added. The reaction was hydrogenated for 20 hr. in a Parr apparatus at 40 psi. After filtration of the catalyst, the solvent was evaporated in vacuo. The thick oil was crystallized from acetone-Skellysolve B (Darco) giving the title compound as white plates (1.6 g, m.p. 100°–102° C.).

$^1$H NMR (CDCl$_3$) 3.81 (t, 2H, J=6 Hz), 3.04 (t, 2H, J=6 Hz), 2.48 (s, 3H), 2.3 (s, 3H), 1.55–2.15 (m, 4H).

Preparation 7

Ethanone, 1-(2-phenylimidazo[1,2-a]pyridin-3-yl) (D-2, Chart 2)

Methanone, (2-methylimidazo[1,2-a]pyridin-3-yl)phenyl- (D-2, Chart 2)

2-Aminopyridine (2.92 g, 31 mole) was dissolved in DMF (15 mL) before the addition of 1-chloro-1-benzoylacetone (6.1 g, 31 mmole). The solution was stirred overnight at room temp. Solvent was removed in vacuo, and the residual oil was diluted with water and extracted with ethyl acetate. Drying of the extracts over sodium sulfate and concentration in vacuo left an oil. Chromatography (silica, 20–30% acetone/Skellysolve B) afforded Ethanone, 1-(2-phenylimidazo[1,2-a]pyridin-3-yl)-(m.p. 110.5°–112.5° C.) and Methanone, (2-methylimidazo[1,2-a]pyridin-3-yl)phenyl- (m.p. 88°–89.5° C.) as the second and third fractions, respectively.

$^1$H NMR (CDCl$_3$) Ethanone, 1-(2-phenylimidazo[1,2-a] pyridin-3-yl)-: 9.77 (d, 1H, J=7 Hz), 7.77 (d, 1H, J=7 Hz), 7.4–7.6 (m, 6H), 7.04 (t, 1H, J=8 Hz), 2.19 (s, 3H); Methanone, (2-methylimidazo[1,2-a]pyridin-3-yl)phenyl: 9.48 (dd, 1H, J=1,7 Hz), 7.4–7.7 (m, 7H), 7.00 (td, 1H, J=2,7 Hz), 2.17 (s, 3H); IR (cm$^{-1}$) Ethanone, 1-(2 -phenylimidazo[1, 2-a]pyridin-3-yl)-: 1622; Methanone, (2-methylimidazo[1, 2-a]pyridin-3-yl)phenyl: 1607.

Preparation 8

[1,2,3]Oxadiazolo[3,4-a]pyridin-8-ium, 3,3α,4,5,6,7-hexahydro-3-oxo-, ylide

To a solution of pipecolinic acid (20.0 g, 0.155 mole) in 1M aq. HCl (16 0 mL) at 0° C. was added solid sodium nitrite (14.5 g. 0.210 mole) in portions. The mixture was stirred at 0° C. for two hours and then extracted with methylene chloride (3×100 mL). The extracts were dried over MgSO$_4$, filtered, and concentrated under vacuum, leaving 14.8 g of yellow oil which crystallized on standing. The crude nitroso compound was dissolved in dry ether (470 mL) and cooled to 0° C. before addition of trifluoroacetic anhydride (15.9 mL, 0.112 mole) via syringe pump over 45 minutes. The reaction was kept under dry nitrogen throughout. During the addition, a crystalline precipitate appeared. The reaction was stirred another 1 hour at the same temp. following addition and then placed in a −20° C. freezer overnight. The crystallized product was collected by filtration, washed with cold ether (100 mL), and dried under a N$_2$ stream followed by vacuum, affording 8.84 g (41% overall) of pure title compound as a cream, microcrystalline powder (m.p. 95°–97° C.).

$^1$H NMR (CDCl$_3$, δ) 4.30 (t, 2H, J=6Hz, NCH$_2$), 2.68 (t, 2H, J=6 Hz, 4-CH$_2$), 1.9–2.2 (m, 4H, CH$_2$); IR (mull, cm$^{-1}$) 1761(b), 1726(b), 1526; UV (ethanol) λ$_{max}$ (ε) 297 (7980); MS m/e (relative intensity) 140 (M$^+$, 22), 82 (100), 55 (86), 54 (31), 40 (28); Analysis calc'd for C$_6$H$_8$N$_2$O$_2$=C, 51.42; H, 5.75; N, 19.99; Found=C, 51.31; H, 5.72; N, 19.73; TLC (silica, 30% EtOAc/hexane) Rf=0.24.

Preparation 9

Ethanone, 1-(4,5,6,7-tetrahydro-2-phenylpyrazolo[1.5-a]pyridin-3-yl)-and regoisomer (B-2, Scheme B)

[1,2,3]Oxadiazolo[3,4-a]pyridin-8-ium, 3,3a,4,5,6,7-hexahydro-3-oxo, ylide (3.0 g, 21.4 mmole) and butynone (4.6 mL, 31.5 mmole) were refluxed in toluene (42 mL) for 8 hours. The reaction mixture was concentrated under reduced pressure and the resulting brown solid contained regioisomers in an 8.4:1 ratio. The reaction mixture was extracted with boiling hexane (14×25 mL) and the extracts cooled overnight to afford white needles which were mostly Ethanone, 1-(4,5,6,7-tetrahydro-2-phenylpyrazolo[1,5-a]pyridin-3-yl)- . The product was further purified by flash chromatography (100 g silica, 30% ethyl acetate/hexane) to produce 2.82 g (56%) of the title compound as the major isomer (m.p. 111°–113° C.). The mother liquor from the hexane extraction/crystallization was concentrated and flash chromatographed (150 g silica, 35% ethyl acetate/hexane) to produce 339 mg (6.7%) of the minor regionisomer (m.p. 122°–124° C.).

Preparation 10

4H-Pyrrolo[1,2- c][1,2,3]oxadiazol-7-ium, 5,6-dihydro-3-hydroxy-, hydroxide, inner salt Prepared as described in: Ranganathan, D.; Bamezai, S. Tet. Lett 1067 (1983).

Preparation 11

Ethanone, 1-(4,5,6,7-tetrahydro-2-propylpyrazolo[1,5-a]pyridin-3-yl)-(B-2, Scheme B)

A solution of [1,2,3]Oxadiazolo[3,4-a]pyridin-8-ium, 3,3a,4,5,6,7-hexahydro-3-oxo, ylide (8.08 g, 57.7 mmole) and 3-hepten-2-one (19.4 g, 173 mmole) in o-xylene (58 mL) was refluxed for 4.5 hrs. The cooled mixture was concentrated in vacuo. The resulting oil was flash chromatographed (350 g silica, 60% ethyl acetate/hexane) to yield 4.15 g of product along with a regioisomer (40% yield). The crude product was recrystallized from hexane to afford 2.44 g (m.p. 44°–45° C.) the title compound as pale yellow needles.

$^1$H NMR (CDCl$_3$) 4.13 (t, 2H, J=6 Hz), 3.06 (t, 2H, J=6 Hz), 2.87 (t, 2H, J=6 Hz), 2.44 (s, 3H), 1.6–2.1 (m, 6H), 1.03 (t, 3H, J=7 Hz); IR (cm$^{-1}$) 1645.

Preparation 12

Ethanone, 1-(2-methylpyrazolo[1,5-a]pyridin-3-yl)-(C-2, Scheme C)

To a solution of 1-amino-2-methylpyridinium iodide (60 g, 250 mmole) in pyridine (57 mL) at 0° C. was added acetyl chloride (36 mL, 510 mmole) dropwise over a 1 hour period. Mechanical stirring was necessary. The reaction mixture was then allowed to come to room temperature and reflux for 15 minutes. The resulting dark liquid was concentrated under vacuum, diluted with ice water (360 mL) and made basic with 3M aq. sodium hydroxide (pH 7.5). Extraction with chloroform (6×400 mL), drying over magnesium sulfate, and concentration of the extracts left 21.4 g of brown liquid. Short column chromatography (900 g silica, 30% ethyl acetate/hexane to 60%) provided 6.59 g (15%) of yellow crystals. Recrystallization from hexane (400 mL) produced 5.15 g (12%) of the title compound as yellow crystals (m.p. 85°–89° C.).

$^1$H NMR (CDCl$_3$, δ) 8.43 (dm, 1H, J=6 Hz, 7-CH), 8.25 (dm, 1H, J=9 Hz, 4-CH), 7.45 (m, 1H, 5-CH), 6.95 (td, 1H,1, 7 Hz, 6-CH), 2.72 (s, 3H, CH$_3$), 2.59 (s, 3H, CH$_3$); IR (mull) 1645, 1638, 1625, 1511, 1504, 1209 cm$^{-1}$; UV (ethanol) λ$_{max}$ (ε) 223 sh (32,630), 226 (36,420), 254 sh (6,190), 260 (6,980), 312 sh (12,050), 318 (12,700), 331 sh (8,740); MS m/e (relative intensity) 174 (M$^+$, 31), 159 (100), 131 (6), 90 (6), 78 (11); Analysis calc'd for C$_{10}$H$_{10}$N$_2$O: C, 68.95; H, 5.79; N, 16.08; Found: C, 68.58; H, 5.66; N, 15.93.

Preparation 13

Ethanone, 1-(5,6,7,8-tetrahydro-2-methylimidazo[1,2-a]pyridin-3-yl)- (E-2, Scheme 1)

Ethanone, 1-(2-methylimidazo[1,2-a]pyridin-3-yl)- (6.1 g, 35 mmole) was dissolved in methanol (76 mL) and 10% Pd/C was added (1.22 g). The reaction mixture was hydrogenated for 6 days on a Parr apparatus at 60 p.s.i. The catalyst was removed by filtration through celite and the reaction mixture was concentrated to produce white crystals. Recrystallization from hexane (150 mL) produced 3.57 g (57%) of the title compound as white crystals (m.p. 89°–90° C.).

$^1$H NMR (CDCl$_3$) δ4.28 (t, 2H, NCH$_2$, J=5.3 Hz), 2 88 (t, 2H, 8-CH$_2$, J=6.0 Hz), 2.54 (s, 3H, CH$_3$), 2.47 (s, 3H, CH$_3$), 1.8–2.1 (m, 4H, CH$_2$); IR (mull) 1636, 1505, 1424, 1401, 1317, 975,964; UV (EtOH) λ$_{max}$ (ε) 272 (14,700), MS m/e (relative intensity) 178 (M$^+$, 43), 164 (9), 163 (100), 150(4), 135 (7); Anal. Calc'd for C$_{10}$H$_{14}$N$_2$O: C, 67.39; H, 7.92; N, 15.72; Found: C, 67.17; H, 8.20; N, 15.55; TLC (SiO$_2$) R$_f$=0.07, ethyl acetate.

Preparation 14

Ethanone, 1-[2-(3,4-dimethoxyphenyl)-4,5,6,7-tetrahydropyrazolo[ 1,5-a]pyridin-3-yl]-(B-2, Scheme B)

Following the procedure described in Preparation 11, but using 4-(3,4 -dimethoxyphenyl)-3-butene-2-one as the enone component there is obtained the title compound (m.p. 165°–167° C.).

$^1$H NMR (CDCl$_3$) 7.02 (d, 1H, J=9 Hz), 7.01 (s, 1H), 6.92 (d, 1H, J=9 Hz), 4.17 (t, 2H, J=6 Hz), 3.93 (s, 3H), 3.91 (s, 3H), 3.09 (t, 2H, J=7 Hz), 2.08 (s, 3H), 1.8–22 (m, 4H); IR (cm$^{-1}$) 1644.

Preparation 15

Ethanone, 1-(2-(2-furanyl)-4,5,6,7-tetrahydropyrazolo[1,5-a]pyridin-3-yl)- (B-2, Scheme B)

Following the procedure described in Preparation 11 but using furfurylidineacetone as the enone component there is obtained the title compound (m.p. 89°–90° C.).

$^1$H NMR (CDCl$_3$) 7.54 (d, 1H, J=2 Hz), 6.86 (d, 1H, J=3 Hz), 6.51 (dd, 1H, J=2,3 Hz), 4.16 (t, 2H, J=7 Hz), 3.09 (t, 2H, J=7 Hz), 2.27 (s, 3H), 1.8–2.1 (m, 4H); IR 1655 cm$^{-1}$.

Preparation 16

Ethanone, 1-[4,5,6,7-tetrahydro-2-(phenoxymethyl)pyrazolo[1,5-a]pyridin-3-yl]-(B-2, Scheme 2)

[1,2,3]Oxadiazolo[3,4-a]pyridin-8-ium, 3,3a,4,5,6,7-hexahydro-3-oxo, ylide (3.0 g, 20.3 mmole) and 5-phenoxypent-3-yne-2-one (9.0 g, 51 mmole) were refluxed in oxylene (20 mL) for 7.5 hrs. Excess reagent and solvent were removed in vacuo. Flash chromatography (300 g silica, 45% ethyl acetate/hexane) provided 5.12 g of the major regioisomer. Recrystallization from hexane gave 4.66 g of white crystals (m.p. 88°–90° C.).

$^1$H NMR (CDCl$_3$) 7.30 (m, 2H), 7.03 (d, 2H, J=8 Hz), 6.97 (t, 1H, J=7 Hz), 5.24 (s, 2H), 4.15 (t, 2H, J=6 Hz), 3.09 (t, 2H, J=6 Hz), 2.47 (s, 3H), 1.8–2.1 (m, 4H); IR 1650 cm$^{-1}$.

Preparation 17

Ethanone, 1-[4,5,6,7-tetrahydro-2-(trimethylsilyl)pyrazolo[1,5a]pyridin-3 -yl]-, (B-2, Chart 2)

Following the procedure described in preparation 16 using 4-trimethylsilyl-3 -butyn-2-one as the ynone component. Flash chromatography (30% ethyl acetate/hexane) provided the major regioisomer as pale yellow crystals. Recrystallization from hexane gave white crystals of the title compound (m.p. 120°–122° C.).

$^1$H NMR (CDCl$_3$) 4.22 (t, 2H, J=6 Hz), 3.06 (t, 2H, J=6 Hz), 2.02 (s, 3H), 1.9–2.1 (m, 4H), 0.31 (s, 9H); IR 1653 cm$^{-1}$.

Preparation 18
Pyridinium, 1-amino-, salt with 2,4,6-trimethylbenzenesulfonic acid To a solution of pyridine (8.1 mL, 100 mmole) in methylene chloride (145 mL) at 0° C. was added a solution of O-mesitylenesulfonylhydroxylamine trifluoroacetic acid salt (CAUTION! Potentially explosive; Tamura et al, *Synthesis* 1 (1977)) (28.75 g, 87.3 mmole) in methylene chloride (145 mL) over a 20 min. period. The reaction mixture was stirred at 30 min. at 0° C. and then diluted with ether (1.6 L). The resulting ppt. was collected by filtration and air-dried to afford the title compound as white crystals (26.69 g, 100%).

$^1$H NMR (CDCl$_3$) 9.04 (d, 2H, J=6 Hz), 8.8–8.9 (bs, 2H), 7.85 (t, 1H, J=8 Hz, 7.63 (t, 2H, J=7 Hz), 6.84 (s, 2H), 2.64 (s, 6H), 2.24 (s, 3H).

Preparation 19
Ethanone, 1-[2-methyl-8-(phenylmethoxy)imidazo[1,2-a] pyridin-3-yl]- (D-2, Scheme D)

Following the procedure described in Preparation 20 with 3-benzyloxy-2-aminopyridine as the pyridine component and recrystallization from ethyl acetate/petroleum ether gave the title compound as brown crystals (m.p. 159°–160° C.).

$^1$H NMR (CDCl$_3$) 9.32 (d, 1H, J=7 Hz), 7.2–7.6 (m, 5H), 6.7–6.9 (m, 2H), 5.38 (s, 2H), 2.83 (s, 3H), 2.63 (s, 3H); IR 1618 cm$^{-1}$.

Preparation 20
Ethanone, 1-(6-chloro-2-methylimidazo[1,2-a]pyridin-3 -yl)- (D-2, Scheme 2)

5-chloro-2-aminopyridine (1.0 g, 7.8 mmole) and 3-chloro-2,4-pentanedione (1.1 g, 7.9 mmole) were refluxed in absolute ethanol (20 mL) for 68 hours. The cooled reaction mixture was diluted with methylene chloride (30 mL) and washed with water (4×50 mL). The organic layers were dried over magnesium sulfate and concentrated to produce 516.5 mg (32%) of a brown solid, pure by NMR. An analytical sample could be obtained by dissolving this material in refluxing hexane to produce the title compound as brown crystals upon cooling (m.p. 165°–168° C.).

$^1$H NMR (CDCl$_3$) δ 9.84 (s, 1H, 5-H), 7.58 (d, 1H, 8-CH, J=10 Hz), 7.43 (dd, 1H, 7-CH, J=9 Hz, 2 Hz), 2.80 (s, 3H, CH$_3$), 2.63 (s, 3H, CH$_3$); IR (mull) 3093, 3073, 3005,1624, 1498, 1492, 1447, 1423, 1412, 1393, 1340, 1324, 1239, 1204, 1057, 976, 827, 739, 691,620, 616, 604 cm$^{-1}$; UV (EtOH) λ$_{max}$ (ε) 219 sh. (19820), 223 (24250), 247 sh. (18440), 254 (23770), 261 (28660), 306 (8330), 317 (8050), 328 sh. (6320); Anal. Calcd for C$_{10}$H$_9$N$_2$OCl: C, 57.57; H, 4.35; N, 13.43; Cl, 16.99; Found: C, 57.64; H, 4.55; N, 13.32; Cl, 17.26; TLC (SiO$_2$) R$_f$=0.66, 10% methanol/chloroform.

Preparation 21
Pyridinium, 1-amino-4-phenyl, iodide (21942-EM-51). (C-1)

4-Phenylpyridine (4.1 g, 26.4 mmole) and hydroxylamine sulfonic acid (1 g, 8.8 mmole) were heated at 100° C. in water (7.5 mL) for 35 minutes. The cooled reaction mixture was treated with potassium carbonate (607 mg, 4.4 mmole) and diluted with absolute ethanol. The solution was then filtered through celite and the filtrate treated with 47% hydrogen iodide (2.2 mL). The reaction mixture was then cooled to −45° C. for one hour. The resulting yellow solid was collected by filtration in a cold filter and washed with cold ether. Suction drying produced 1.58 g (61%) of the title compound as yellow crystals, pure by NMR.

$^1$H NMR (CDCl$_3$) δ 8.82 (d, 2H, 2,6-pyridine-H, J=7 Hz), 8.3–8.5 (m, 2H, 3,5-pyridin-H), 7.9–8.1 (m, 2H, phenyl-H), 7.5–7.8 (m, 3H, phenyl-H).

Preparation 22
Ethanone, 1-(7,8,9,10-tetrahydro-2-methylimidazo[2,1-a] isoquinolin-3 -yl)- (D-2, Scheme D)

Following the procedure of Preparation 20 with 1-amino-5,6,7,8-tetrahydroisoquinoline as the pyridine component. Recrystallization from hexane provided the title compound as red crystals (m.p. 91°–93° C.).

$^1$H NMR (CDCl3) 9.44 (d, 1H, J=7 Hz), 6.73 (d, 1H, J=7 Hz), 3.05 (m, 2H), 2.8 (m, 5H), 2.60 (s, 3H), 1.8–2.0 (m, 4H); IR 1631 cm$^{-1}$.

Preparation 23
Ethanone, 1-(2-methyl-5phenylpyrazolo[1,5-a]pyridin-3 -yl)- (C-2, Scheme C)

4-Phenyl-N-aminopyridinium iodide (39.33 g, 0.132 mole), 2,4-pentanedione (27 mL, 0.264 mole) and potassium carbonate (62 g) were heated at 80° C. for 2 hours in water (224 mL). The cooled reaction mixture was diluted with ether (500 mL), washed with water (200 mL) and 1.0M hydrochloric acid (3×200 mL) to remove 4-phenylpyridine, and dried over magnesium sulfate. The organic layers were concentrated to produce 14.9 g of yellow crystals. An analytical sample was prepared by dissolving this material in refluxing ethyl acetate and petroleum ether (8:10 ratio). Cooling produced the title compound as brown crystals (m.p. 109°–111° C.).

$^1$H NMR (CDCl$_3$) δ 8.4–8.5 (m, 2H, 4,7-pyridine-H), 7.70 (d, 2H, phenyl-H, J=8 Hz), 7.4–7.6 (m, 3H, phenyl-H), 7.20 (dd, 1H, 6-CH, J=7 Hz, 2 Hz), 2.78 (s, 3H, CH$_3$), 2.60 (s, 3H, CH$_3$); IR (mull) 1653, 1631, 1529, 1508, 1501, 1495, 1448, 1407, 1360, 1221, 1203, 1079, 767, 695, 607 cm$^{-1}$; UV (EtOH) λ$_{max}$ (ε) 240 sh. (25620), 251 (30410), 269 (17040), 338 (15500); MS m/e (relative intensity) 251 (8), 250 (42, M$^+$), 236 (17), 235 (100), 166 (6); Anal. Calcd for C$_{16}$H$_{14}$N$_2$O: C, 76.78; H, 5.64; N 11.19; Found: C, 76.61; H, 5.61; N, 11.17; TLC (SiO$_2$) R$_f$=0.61, 60% ethyl acetate/hexane.

Preparation 24
Ethanone, 1-(2-methylimidazo[2, 1-a]isoquinolin-3-yl)- (D-2, Scheme D)

Following the procedure of Preparation 20 with 1-aminoisoquinoline as the pyridine component and recrystallization from ethanol/water afforded the title compound as pink crystals (m.p. 172°–173° C.).

$^1$H NMR (CDCl$_3$) 9.42 (d, 1H, J=8 Hz), 8.6–8.7 (m, 1H), 7.7 (m, 3H), 7.23 (d, 1H, J=8 Hz), 2.85 (s, 3H), 2.66 (s, 3H); IR (mull) 1636 cm$^{-1}$.

Preparation 25
Ethanone, 1-[2-methyl-5-(phenylmethyl)pyrazolo[1,5-a]pyridin-3-yl]- (C-2, Scheme C)

Following the procedure of Preparation 23 starting with 4-benzylpyridine and recrystallization from hexane provided yellow the title compound as crystals (m.p. 77°–78° C.).

$^1$H NMR (CDCl$_3$) 8.29 (d, 1H, J=7 Hz), 8.12 (s, 1H), 7.3–7.5 (m, 5H), 6.72 (dd, 1H, J=2,7 Hz), 4.06 (s, 2H), 2.69 (s, 3H), 2.55 (s, 3H); IR (mull) 1643, 1627 cm$^{-1}$.

Preparation 26
Acetamide, N-(3-acetyl-2-methylimidazo[1,2-a]pyridin-8-yl )-

2,3-Diaminopyridine (28 g, 0.256 mole) and acetic anhydride (30 mL, 0.38 mole) were stirred at room temp in methylene chloride (770 mL) for 30 min. The mixture was concentrated in vacuo to a brown solid. Recrystallization from methylene chloride/hexane (10/1) gave off-white crystals (21.9 g, 57%) of 3-acetamido-2-aminopyridine. This acetamide was combined with 3-chloro-2,4-pentanedione (20 g, 0.146 mole) in abs. ethanol (350 mL) and stirred under reflux for 20 hrs. After cooling, the mixture was diluted with methylene chloride (300 mL) and washed with water (3×300 mL). The organic phase was dried over magnesium sulfate and concentrated to a green solid. Recrystallization from methylene chloride/hexane (1/1) gave the title compound as green crystals (7.3 g, 21%. m.p. 173°–175° C.).

$^1$H NMR (CDCl3) 9.36 (d, 1H, J=7 Hz), 8.55 (bs, 1H), 8.39 (d, 1H, J=8 Hz), 698 (t, 1H, J=7 Hz), 2.78 (s, 3H), 2.62 (s, 3H), 2.31 (s, 3H); IR (mull) 1669, 1636, 1632 cm$^{-1}$.

Preparation 27

Ethanone, 1-(6-bromo-2-methylimidazo[1,2-a]pyridin-3-yl)- (D-2, Scheme D)

4-Bromo-2-aminopyridine (20 g, 0.12 mole) and 3-chloro-2,4-pentanedione (16.0 g, 0.117 mole) were stirred in abs. ethanol (300 mL) under reflux for 4 days. The cooled reaction was diluted with methylene chloride (300 mL) and washed with water (3×300 mL). The organic layer was dried and concentrated to a dark solid. Recrystallization from hexane gave the title compound as yellow crystals (m.p. 167°–168° C.).

$^1$H NMR (CDCl$_3$) 9.77 (s, 1H), 7.7–7.8 (m, 2H), 2.72 (s, 3H), 2.60 (s, 3H); IR (mull) 1631 cm$^{-1}$.

Example 1

Ethanone, 1-(5,6,7,8-tetrahydro-2-methyl-4H-pyrazolo[1,5-a]azepine-3-yl)-, oxime (A-3, Scheme A)

Hydroxylamine hydrochloride (20.85 g, 0.30 mole) and Ethanone, 1-(5,6,7,8 -tetrahydro-2-methyl-4H-pyrazolo[1,5-a]-azepin-3-yl)- (48.0 g, 0.25 mole) were stirred in a refluxing solution of ethanol (450 mL) and pyridine (150 mL) for 22 hrs. Solvent was removed in vacuo, leaving a thick slurry. Water (150 mL) was added, and the mixture was extracted with methylene chloride (1×250 mL, 1×100 mL). The organics were washed with brine (50 mL) and dried over magnesium sulfate. Concentration in vacuo left a solid which was dissolved in methylene chloride (150 mL) at reflux before the addition of hexane (300 mL). Cooling to room temp. provided 37.85 g (m.p. 136°–150° C.) of a mixture of oxime isomers with the title compound being the major isomer (8/1).

$^1$H NMR (CDCl$_3$) Major isomer. 4.20 (m, 2H), 2.81 (m, 2H), 2.26 (s, 3H), 2.18 (s, 3H) 1.6–1.9 (m, 6H); Analysis calc'd for $C_{11}N_{17}N_3O$=C, 63.74; H, 8.27; N, 20.27; Found=C, 63.62; H. 8.52; N, 20.03.

Example 2

Ethanone, 1-(4,5,6,7-tetrahydro-2-methylpyrazolo[1,5-a]pyridin-3-yl)-, oxime (B-3, Scheme 3)

A solution of Ethane, 1-(4,5,6,7-tetrahydro-2-methylpyrazolo[1,5-a]-pyridin-3-yl)- 1.56 g, 8.75 mmole) and hydroxylamine hydrochloride (0.73 g, 10.5 mmole) in absolute ethanol (16 mL) and pyridine (5.5 mL) was refluxed for 24 hours. Most of the solvent was removed under vacuum after cooling. The residue was partitioned between water (25 mL) and methylene chloride (30 mL) and the aqueous phase further extracted with methylene chloride (2×20 mL). The combined organics were dried over MgSO$_4$ and concentrated to give a crystalline solid which was dissolved in methylene chloride (20 mL) at reflux and then diluted with hexane (60 mL). Cooling to 0° gave the title compound as off-white prisms (1.44 g, 85%) (m.p. 150°–153° C.).

$^1$H NMR (CDCl$_3$, δ) 9.40 (bs,1H, NOH), 4.09 (t, 2H, J=6 Hz, NCH$_2$), 2.83 (s, 3H, J=6 Hz, pyrazole-CH$_2$), 2.33 (s, 3H, CH$_3$), 2.20 (s, 3H, CH$_3$), 1.95–2.1 (m, 2H, CH$_2$), 1.77–1.95 (m, 2H, CH$_2$); IR (mull) 3194, 1630, 920 cm$^{-1}$; UV (ethanol) $\lambda_{max}$ (ε) 203 (11500), 238 (9700); MS m/e (rel. intens.) 193 (M$^+$, 39), 176 (100), 148 (77), 135 (21), 133 (15), 77 (15), 65 (20), 42 (35); Analysis calc'd for $C_{10}H_{15}N_3O$=C, 62.15; H, 7.82; N, 21.74; Found=C, 61.83; H, 8.01; N, 21.72

Example 3

Ethanone, 1-(5,6,7,8-tetrahydro-2-methyl-4H-pyrazolo[1,5-a]azepine-3-yl)-, acetoxime A solution of Ethanone, 1-(5,6,7,8-tetrahydro-2-methyl-4H-pyrazolo-[1,5-a]azepine-3-yl)-, oxime (2.49 g, 12 mmole) and acetic anhydride (2.88 mL, 36 mmole) in methylene chloride (36 mL) was stirred at room temp. for 1.5 hours. The reaction mixture was diluted with water (50 mL) and extracted with methylene chloride (2×50 mL). The extracts were dried over MgSO$_4$ and concentrated to afford a pale yellow oil, which was purified by elution through a short column of silica (150 g, 70–230 mesh, 60% ethyl acetate/hexane) yielding 2.85 g (95%) of the title compound as a colorless oil which crystallized on standing. An analytical sample could be obtained by recrystallization from hexane (m.p. 68°–70° C.).

$^1$H NMR (CDCl$_3$, δ) 4.2 (m, 2H, NCH$_2$), 2.95 (m, 2H, pyrazole-CH$_2$), 2.29 (s, 6H, CH$_3$), 2.25 (s, 3H, CH$_3$), 1.6–1.9 (m, 6H, CH$_2$); IR (mull) 1765, 1606, 1546, 1493, 1441, 1367, 1208, 928, 754 cm$^{-1}$; UV (ethanol) $\lambda_{max}$ (ε) 250 (9430); MS m/e (rel. intens.) 249 (M$^+$, 11), 190 (100), 189 (94), 188(67), 174 (32), 161 (47); Exact mass calc'd for $C_{13}H_{19}N_3O_2$=249.1477; Found=249.1477; TLC (silica, 10% methanol/chloroform) Rf 0.82.

Example 4

Ethanone, 1-(4,5,6,7-tetrahydro-2-phenylpyrazolo[1,5-a]pyridin-3-yl)-, oxime (A-3, Scheme A)

Ethanone, 1-(4,5,6,7-tetrahydro-2-phenylpyrazolo[1,5-a]pyridin-3-yl)- ( 2.27 g, 9.45 mmole) and hydroxylamine hydrochloride (788 mg, 11.34 mmole) were refluxed in absolute ethanol (17 mL) and pyridine (6 mL) for 3 hours. The reaction mixture was diluted with water (50 mL) and extracted with methylene chloride (4×50 mL). The organic layers were dried over magnesium sulphate and concentrated to produce white crystals. These were recrystallized from a methylene chloride/hexane solution (25:10 mL) to produce 1.60 g (66%) of white crystals with a 5:1 ratio of anti:syn isomers, title compound, (m.p 178°–181° C.). A second crop produced 0.53 g (22%) of white crystals.

NMR of Major Isomer and UV, IR, MS, Elemental of Mixture $^1$H NMR (CDCl$_3$)δ 8.2–8.3 (s, 1H, OH), 7.5–7.7 (m, 2H, phenyl-H), 7.3–7.5 (m, 3H, phenyl-H), 4.22 (t, 2H, J=6 Hz, NCH$_2$), 2.89 (t, 2H, J=6 Hz, 4-CH$_2$), 1.95 (s, 3H, CH$_3$), 1.8–2.2 (m, 4H, CH$_2$); IR (mull) 3195, 1626, 1545, 1503, 1447, 912, 778 cm$^{-1}$; UV (EtOH) $\lambda_{max}$ (ε) 232 (15750), 250 (14250); MS m/e (relative intensity) 255 (M$^+$, 73), 254 (62), 239 (19), 238 (100), 210 (36); Anal. Calcd for $C_{15}H_{17}N_3O$: C, 70.56; H, 6.71; N, 16.46; Found: C, 70.73; H, 7.03; N, 16.43; TLC (SiO$_2$) Rf=0.46, 30% ethyl acetate/chloroform.

Minor Isomer $^1$H NMR (CDCl$_3$, δ) 4.24 (t, 2H, NCH$_2$), 2.78 (t, 2H, 4-CH$_2$), 1.97 (s, 3H, CH$_3$)—only peaks visible in NMR.

Example 5

Ethanone, 1-(5,6,7,8-tetrahydro-2-methyl-4H-pyrazolo[1,5-a]azepin-3-yl)-, O-(2 -hydroxyethyl)-oxime A mixture of Ethanone, 1-(5,6,7,8-tetrahydro-2-methyl-4H-pyrazolo[1,5-a] -azepin-3-yl)- (4.42 g, 23.0 mmole), O-(2-hydroxyethyl)hydroxylamine (3.54 g, 45.9 mmole), acetic acid (2.6 mL) and pyridine (3.7 mL) in absolute ethanol (26 mL) was refluxed for 4 hours. The reaction mixture was concentrated under reduced pressure and partitioned between water (100 mL) and methylene chloride (100 mL). The aq. phase was further extracted with methylene chloride (3×100 mL) and the combined organic extracts were dried over $MgSO_4$ and concentrated to produce a colorless liquid. Column chromatography (300 g silica, 70–230 mesh, 80% ethyl acetate/hexane) afforded 5.61 g (97%) of the title compound as a viscous, colorless oil.

$^1$H NMR (CDCl$_3$, δ) 4.1–4.3 (m, 4H, NCH$_2$, NOCH$_2$), 3.9 (m, 2H, CH$_2$OH), 2.8 (m, 2H, pyrazole-CH$_2$), 2.26 (s, 3H, CH$_3$), 2.17 (s, 3H, CH$_3$), 1.6–1.9 (m, 6H, CH$_2$); IR (mull) 3350, 1605, 1553, 1441, 1364, 1356, 1081, 1079, 1048 cm$^{-1}$; UV (ethanol) $\lambda_{max}$ (ε) 231 (8280); MS m/e (rel. intens.) 251 (M$^+$, 100), 191 (88), 190 (100), 149 (59); Exact mass calc'd for $C_{13}H_{21}N_3O_2$=251.1634; Found=251.1629; TLC (silica, 80% ethyl acetate/hexane) Rf 0.25.

Example 6
Ethanone, 1-(5,6-dihydro-2-methyl-4H-pyrrolo[1,2-b]pyrazol-3-yl)-, oxime (A-3, Scheme A)

Ethanone, 1-(5,6-dihydro-2-methyl-4H-pyrrolo[1,2-b] pyrazol-3-yl)-( 1.60 9, 9.74 mmole) and hydroxylamine hydrochloride (6.72 g, 97.4 mmole) were refluxed in absolute ethanol (94 mL) and pyridine (31 mL) for 6.5 hours. The excess reagents were removed under reduced pressure and the reaction mixture was diluted with water (100 mL) and extracted with methylene chloride (3×100 mL). The organic layers were dried over magnesium sulphate and concentrated to produce pale yellow crystals. This was dissolved in refluxing methylene chloride (100 mL) and hexane (25 mL) was added to produce 0.93 g (53%) title compound as a powdery white material (m.p. 190°–192° C.) after cooling to 0° C.

$^1$H NMR (CDCl$_3$)δ 4.11 (t, 2H, J=7 Hz, NCH$_2$), 3.02 (t, 2H, J=8 Hz, pyrazole-CH$_2$), 2.61 (m, 2H, CH$_2$), 2.42 (s, 3H, CH$_3$), 2.21 (s, 3H, CH$_3$); IR (mull) 3157, 1663, 1632, 1554, 1530, 1510, 989; UV (EtOH) $\lambda_{max}$ (ε) 239 (11700); MS m/e (relative intensity) 179 (M$^+$, 66), 163 (11), 162 (100), 133 (17); Anal. Calcd for $C_9H_{13}N_3O$: C, 60.32; H, 7.31; N, 23.45; Found: C, 60.20; H, 7.46; N, 23.47; TLC (SiO$_2$) R$_f$=0.48, 10% methanol/chloroform.

Example 7
Ethanone, 1-(3-methylimidazo[1,5-a]pyridin-1-yl)-,oxime (F-3, Scheme F)

Ethanone, 1-(3-methylimidazo[1,5-a]pyridin-1-yl)-(J. D. Bower, G. L. Ramage *J. Chem. Soc.* 2834 (1955)) (2.0 g, 11.5 mmole) and hydroxylamine hydrochloride (958 mg, 13.8 mmole) were refluxed in absolute ethanol (23 mL) and pyridine (7.7 mL) for 16 hours. The reaction mixture was diluted with water (150 mL) and, after shaking, a yellow solid formed. This solid was collected by filtration. The filtrate was then extracted with methylene chloride (3×100 mL). The organic phase was dried over magnesium sulphate and concentrated to produce a yellow oil. The yellow oil and the collected solid were combined and dissolved in boiling 95% ethanol (60 mL) and water (36 mL) was added to produce 2.08 g (96%) of yellow title compound as crystals (m.p. 159°–160° C.) after cooling.

$^1$H NMR (CDCl$_3$) δ 8.03 (dt, 1H, 5-CH, J=8.6, 0.7 Hz), 7.71 (dt, 1H, 8-CH, J=6.8, 0.7 Hz), 6.85 (m, 1H, 7-CH), 6.69 (m, 1H, 6-CH), 2.69 (s, 3H, CH$_3$), 2.50 (s, 3H, CH$_3$); IR (mull) 3470, 1637, 1533, 1528, 1445, 994, 983, 750 cm$^{-1}$; UV (EtOH) $\lambda_{max}$ (ε) 224 (15,530), 265 sh (4,440), 297 sh (7,630), 304 (8,210), 315 sh (6,160), 365 (4,220); MS m/e (relative intensity) 189 (M$^+$, 100), 172 (78), 131 (41), 117 (23), 105 (69); Exact Mass Calc'd for $C_{10}H_{11}N_3O$: 189.0902; Found: 189.0898; TLC (SiO$_2$) R$_f$=0.44, 10% methanol/chloroform.

Example 8
Ethanone, 1-(5,6,7,8-tetrahydro-3-methylimidazo[1,5-a]pyridin- 1-yl)-, oxime, monohydrochloride (F-3, Scheme F)

A solution of ketone Ethanone, 1-(5,6,7,8-tetrahydro-3-methylimidazo[1,5a]pyridin-1-yl)- (0.80 9, 4.5 mmole) and hydroxylamine hydrochloride (0.38 g, 5.4 mmole) in absolute ethanol (9 mL) and pyridine (3 mL) was refluxed for 2 hours. The initially homogenous solution deposited a crystalline precipitate during the reaction. After cooling to room temperature, the precipitate was collected by suction filtration and washed with absolute ethanol. Drying under vacuum left 742 mg (85%) the title compound as a white microcrystalline solid that was analytically pure [m.p. 265° C. (dec.)].

$^1$H NMR (DMSO d6, δ) 11.61 (1H, s, OH), 4.04 (t, 2H, J=6 Hz, NCH$_2$), 2.92 (t, 2H, J=6 Hz, 8-CH$_2$), 2.59 (s, 3H, CH$_3$), 2.20 (s, 3H, CH$_3$), 1.7–2.0 (m, 4H, CH$_2$); IR (mull, cm$^{-1}$) 3102, 1691, 1633, 1563, 1004, 927, 857; UV (ethanol) $\lambda_{max}$ (ε) 242 sl. sh (8,730), 252 (9,230); MS m/e (relative intensity) 193 (M$^+$ of free base, 57), 176 (100), 160 (19), 159 (61); Analysis calc'd for $C_{11}H_{16}N_3OCl$: C, 52.29; H, 7.02; N, 18.29; Cl, 15.43; Found: C. 52.39;H, 7.17; N, 18.28; Cl, 15.91.

Example 9
Ethanone, 1-(4,5,6,7-tetrahydro-2-propylpyrazolo[1,5-a]pyridin-3-yl)-, oxime) (B-3, Scheme B )

Ethanone, 1-(4,5,6,7-tetrahydro-2-propylpyrazolo[ 1,5-a] pyridin-3-yl)- ( 1.64 g, 7.9 mmole) and hydroxylamine hydrochloride (663 mg, 9.5 mmole) were refluxed in absolute ethanol (16.4 mL) and pyridine (8.2 mL) for 5 hours. The clear reaction mixture was diluted with water (50 mL) and extracted with methylene chloride (5×50 mL). The organic layers were dried over magnesium sulphate and concentrated to produce a yellow oil. This was dissolved in methylene chloride (2 mL) and hexane (8 mL) was added to produce 1.12 g (64%) the title compound as white crystals (m.p. 106°– 109° C.) after cooling to 0° C.

$^1$H NMR (CDCl$_3$)δ 4.11 (t, 2H, NCH$_2$, J=5.6 Hz), 2.83 (t, 2H, 4-CH$_2$, J=5.8 Hz) 2.69 (t, 2H, CH$_2$-Et, J=6.8 Hz), 2.20 (s, 3H, oxime-CH$_3$), 1.5–2.0 (m, 6H, CH$_2$), 0.98 (t, 3H, CH$_3$, J=6.4 Hz); IR (mull) 3181, 1600, 1528, 1503, 1402, 1003, 921, 901, 743; UV (EtOH) $\lambda_{max}$ (ε) 238 (9470); MS m/e (relative intensity) 221 (M$^+$, 23), 204 (100), 189 (19), 176 (11); Anal. Calcd for $C_{12}H_{19}N_3O$: C, 65.13; H, 8.65; N, 18.99; Found: C, 64.81; H, 8.54; N, 19.08; TLC (SiO$_2$) R$_f$=0.39, 10% methanol/chloroform.

Example 10
Ethanone, 1-(2-methylpyrazolo[1,5-a]pyridin-3-yl)-, oxime (C-3, Scheme C)

Ethanone, 1-(2-methylpyrazolo[1,5-a]pyridin-3-yl)- (2.65 g, 15.2 mmole) and hydroxylamine hydrochloride (2.11 g, 30.4 mmole) were refluxed in absolute ethanol (29 mL) and pyridine (16 mL) for 7 hours. The cooled reaction mixture was diluted with water (50 mL) and extracted with methylene chloride (5×50 mL). The organic layers were dried over magnesium sulphate and concentrated to produce a yellow solid, which was dissolved in refluxing methylene chloride (65 mL) and hexane (65 mL) was added to produce 1.32 g (46%) the title compound as yellow crystals (m.p. 126°–128° C.) upon cooling.

$^1$H NMR (CDCl$_3$) δ 8.8–9.1 (s, 1H, OH), 8.43 (d, 1H, NCH, J=7.0 Hz), 7.78 (d, 1H, 4-CH, J=9.0 Hz), 7.19 (m, 1H, 5-H), 6.76 (td, 1H, 6-H, J=6.5, 1.2 Hz), 2.63 (s, 3H, CH$_3$), 2.40 (s, 3H, CH$_3$); IR (mull) 3250, 3221, 1636, 1431, 1361, 1353, 1226, 937, 912, 753 cm$^{-1}$; UV (EtOH) $\lambda_{max}$ (ε) 130 (26,130), 253 (8,230), 261 sh. (7,120), 300 (6,070), 317 sh (4,290); MS m/e (relative intensity) 189 (100), 172 (26), 157

(38), 132 (85), 105 (81); Anal. Calc'd for $C_{10}H_{11}N_3O$: C, 63.48; H, 5.86; N, 22.21; Found: C, 63.61; H, 5.80; N, 21.94; TLC (SiO$_2$) R$_f$=0.80, 10% methanol/chloroform.

Example 11

Ethanone, 1-(2-methylimidazo[1,2-a]pyridin-3-yl), oxime (D-3, Scheme D)

Ethanone, 1-(2-methylimidazo[1,2-a]pyridin-3-yl)- (3.6 g, 20.6 mmole) and hydroxylamine hydrochloride (1.7 g, 24.7 mmole) were refluxed in absolute ethanol (41 mL) and pyridine (14 mL) for 16 hours. Water (150 mL) was added to the cooled solution and the white solid that precipitated was collected by filtration. The filtrate was extracted with chloroform (8×100 mL) and ethyl acetate (2×100 mL). The organic layers were dried over magnesium sulphate and concentrated to produce white crystals. The collected solid and the extracted solid were combined and dissolved in boiling 95% ethanol (70 mL) and water (50 mL) was added to produce 2.38 g (61%) of the title compound as white flocculent material (m.p. 206°–208° C.) after cooling.

$^1$H NMR (CDCl$_3$) δ 9.03 (dt, 1H, 5-CH, J=6.9, 1.4 Hz), 8.8–9.0 (bs, 1H, OH), 7.61 (bd, 1H, 8-CH, J=9.4 Hz), 7.24 (m, 1H, 7-CH), 6.82 (bt, 1H, J=8 Hz, 6-CH), 2.67 (s, 3H, CH$_3$), 2.46 (s, 3H, CH$_3$); IR (mull) 3127, 1637, 1504, 1444, 1358, 1291, 1027, 936 cm$^{-1}$; UV (EtOH) λ$_{max}$ (ε) 209 (21,090), 218 sh (17,000), 242 sh (15,160), 249 (19,020), 256 (19,300), 301 (7,960); MS m/e (relative intensity) 189 (M$^+$, 100), 172 (93), 157 (33), 132 (85), 78 (68); Exact Mass Calc'd for $C_{10}H_{11}N_3O$=189.0902; Found=189.0919; TLC (SiO$_2$) R$_f$=0.34, 10% methanol/chloroform, UV active.

Example 12

Ethanone, 1-(2-(2-furanyl)-4,5,6,7-tetrahydropyrazolo[1,5-]pyridin-3-yl)-, oxime (B-3, Scheme B )

Ethanone, 1-[2-(2-furanyl)-4,5,6,7-tetrahydropyrazolo[1,5-a]pyridin-3-yl]- (2.29 g, 9.94 mmole) and hydroxylamine hydrochloride (823 mg, 11.9 mmole) were refluxed in absolute ethanol (20 mL) and pyridine (6.7 mL) for 3.5 hours. The cooled reaction mixture was diluted with water (50 mL) and the resulting white precipitate was collected by filtration. The filtrate was extracted with methylene chloride (3×50 mL), dried over magnesium sulphate and concentrated to produce a brown oil. The oil and the solid were combined and recrystallized from 95% ethanol (25 mL) and water (15 mL) to produce 1.60 g (66%) of pale yellow crystals, containing a 9:1 ratio of oxime isomers. An analytical sample of the title compound was prepared by a second recrystallization from 95% ethanol and water (m.p. 150°–153° C.).

$^1$H NMR (CDCl$_3$, δ) 8.55 (bs, 1H, OH), 7.46 (d, 1H, 5-furan-H, J=1.9 Hz), 6.60 (d, 1H, 3-furan H, J=3.3 Hz), 6.44 (dd, 1H, 4-furan-H, J=1.8, 3.3 Hz), 4.18 t, 2H, NCH$_2$, J=6.1 Hz), 2.84 (t, 2H, 4-CH$_2$, J=6.3 Hz), 2.09 (s, 3H, CH$_3$), 1.8–22 (m, 4H, CH$_2$); IR (mull) 3298, 3209, 3186, 3096, 1651, 1558, 1514, 1448, 1438, 1404, 1326, 1217, 1180. 1008, 907, 753 cm$^{-1}$; UV (EtOH) λ$_{max}$ (ε) 233 (12260), 265 (13800); MS m/e (relative intensity) 245 (M$^+$, 100), 228 (62), 216 (27), 200 (58), 188 (19); Exact Mass Calcd for $C_{13}H_{15}N_3O_2$=245.1164; Found=245.1166; TLC (SiO$_2$) R$_f$=0.25, 40% ethyl acetate/hexane.

Example 13

Ethanone, 1-(2-(3,4-dimethoxyphenyl)-4,5,6,7-tetrahydropyrazolo[1.5-a]-pyridin-3-yl)-oxime (B-3, Scheme B)

Ethanone, 1-[2-(3,4-dimethoxyphenyl)-4,5,6,7-tetrahydropyrazolo[1,5-a]pyridin-3-yl]- (3.5 g. 11.9 mmole) and hydroxylamine hydrochloride (1.0 g, 14.3 mmole) were refluxed in absolute ethanol (24 mL) and pyridine (7.8 mL) for 4.5 hours. The cooled reaction mixture was diluted with water (250 mL) and the resulting yellow solid was collected by filtration. The filtrate was extracted with methylene chloride (3×250 mL). The organic layers were dried over magnesium sulphate and concentrated to produce a yellow oil. The solid and the oil were combined and dissolved in boiling 95% ethanol (55 mL) and water (25 mL) was added. Cooling produced 1.94 g (52%) of white crystals, which contained a 7:1 mixture of oxime isomers. An analytical sample of the title compound was prepared by a second recrystallization from 95% ethanol/water (m.p. 153°–155° C.).

$^1$H NMR (CDCl$_3$)δ 8.0–8.1 (s, 1H, OH), 7.15 (d, 1H, 2-phenyl-H, J=1.7 Hz), 7.07 (dd, 1H, 6-phenyl-H, J=7.9, 1.7), 6.88 (d, 1H, 5-phenyl-H, J=8.5 Hz), 4.19 (t, 2H, NCH$_2$, J=6.2 Hz), 3.91 (s, 3H, OCH$_3$), 3.90 (s, 3H, OCH$_3$), 2.88 (t, 2H, 4-CH$_2$, J=6.8 Hz), 2.0–2.1 (m, 2H, 6-CH$_2$), 1.95 (s, 3H, oxime-CH$_3$), 1.8–1.9 (m, 2H, 5-CH$_2$); IR (mull) 3310, 3176, 1645, 1606, 1585, 1548, 1433, 1262, 1229, 1140, 1025, 939 cm$^{-1}$; UV (EtOH) λ$_{max}$ (ε) 208 (31100), 259 (14320), 285 (7000); MS m/e (relative intensity) 315 (M$^+$, 18), 298 (34), 299 (8), 282 (5), 44 (100); Exact Mass Calcd for $C_{17}H_{21}N_3O_3$=315.1583; Found=315.1564; TLC (SiO$_2$) R$_f$=0.20,10% methanol/chloroform.

Example 14

Ethanone, 1-(2-phenoxymethyl-4,5,6,7-tetrahydropyrazo[1,5-a]pyridin-3-yl)-, oxime (B-3, Scheme 3)

Ethanone, 1-[4,5,6,7-tetrahydro-2-(phenoxymethyl)pyrazolo[1,5-a]pyridin-3-yl]-( 2.5 g, 9.3 mmole) and hydroxylamine hydrochloride (771 mg, 11.1 mmole) were refluxed in absolute ethanol (15 mL) and pyridine (7.7 mL) for 6 hours. The reaction mixture was diluted with water (100 mL) and the result in a white solid that precipitated was collected by filtration. The filtrate was extracted with methylene chloride (4×100 mL), the organic layers dried over magnesium sulphate and concentrated to produce a clear oil. The oil and the solid were combined and recrystallized from methylene chloride/hexane (1.7/1,200 mL) to produce 1.81 g (69%) of the title compound as white crystals (m.p. 192°–194° C.).

$^1$H NMR (CDCl$_3$)δ 7.81 (s, 1H, OH), 7.27 (t, 2H, J=8 Hz, Ph-H (meta)), 7.00 (d, 2H, J=8 Hz, Ph-H (ortho)), 6.94 (t, 1H, J=8 Hz, Ph-H (para)), 5.08 (s, 2H, pyrazole-CH$_2$), 4.15 (t, 2H, NCH$_2$, J=6.0 Hz), 2.86 (t, 2H, 4-CH$_2$, J=6.3 Hz), 2.21 (s, 3H, CH$_3$), 1.8–2.1 (m, 4H, CH$_2$), IR (mull) 3202, 1626, 1598, 1585, 1496, 1237, 1222, 1010, 922, 758 cm$^{-1}$, UV (EtOH) λ$_{max}$ (ε) 221 (16200), 235 (10200), 263 sl. sh. (2730), 270 (2010), 277 (1430); MS m/e (relative intensity) 285 (M$^+$, 8), 268 (9), 92 (100), 175 (20), 170 (17); Anal. Calcd for $C_{16}H_{19}N_3O_2$: C, 67.35; H, 6.71; N, 14.73; Found: C, 67.30; H, 6.69; N, 14.68; TLC (SiO$_2$) Rf=0.48, 10% methanol/chloroform.

Example 15

Ethanone, 2-(phenylthio)-1-(5,6,7,8-tetrahydro-2-methyl-4H-pyrazolo[ 1,5-a]azepin-3-yl)-, oxime (A-4, Scheme A)

To a solution of Ethanone, 1-(5,6,7,8-tetrahydro-2-methyl-4H-pyrazolo-[1,5a]azepine-3-yl)-, oxime (540 mg, 2.6 mmole) in THF (13 mL) at −78° C. was added n-BuLi (1.7M in hexane, 3 mL, 5.2 mmole). The solution was stirred for 30 min. at −78° C. and then at 0° C. for 1 hr. After cooling back down to −78° C., diphenyldisulfide (568 mg, 2.6 mmole) in THF (2 mL) was added slowly. The reaction was allowed to stir at that temp for 10 min and then warmed to room temp. The reaction was quenched with sat. sodium bicarbonate (25 mL) and extracted with ether. The extracts were dried over magnesium sulfate and concentrated to afford a semi-solid (975 mg). Flash chrom. (50 g silica, 80% ethyl acetate/hexane) gave 614 mg of the title compound as a 4/1 mixture of oxime isomers.

Analysis calc'd for $C_{17}H_{21}N_3OS$=C, 64.73; H, 6.71; N, 13.32; S, 10.16; Found=C, 64.47; H, 6.76; N, 13.00; S, 10.22; $^1$H NMR (CDCl3) 8.45 (bs, 1H), 7.1–7.3 (m, 5H), 4.15 (m, 2H), 4.10 (s, 2H), 2.6 (m, 2H), 2.17 (s, 3H), 1.4–1.8 (m, 6H).

Example 16

Ethanone, 1-(4,5,6,7-tetrahydro-2-trimethylsilylpyrazolo[1,5-a]pyridin-3-yl)-, oxime (B-3, Scheme B )

Ethanone, 1-[4,5,6,7-tetrahydro-2-(trimethylsilyl)pyrazolo[ 1,5-a]pyridin-3-yl]- ( 3.0 g, 12.5 mmole) and hydroxylamine hydrochloride (1.3 g, 18.7 mmole) were refluxed in absolute ethanol (20 mL) and pyridine (10 mL) for 7 hours. The reaction mixture was diluted with water (100 mL) and the white solid that precipitated was collected by filtration. The filtrate was extracted with methylene chloride (3×100 mL), the organic layers were dried over magnesium sulfate and concentrated to produce a pink solid. The solids were combined and recrystallized from 95% ethanol/water (1.5/1, 25 mL) to afford 2.00 g (64%) of the title compound as white needles (m.p. 167°–168° C.).

$^1$H NMR (CDCl$_3$)δ 4.19 (t, 2H, NCH$_2$, J=5.9 Hz), 2.80 (t, 2H, 4-CH$_2$, J=6.4 Hz), 2.15 (s, 3H, oxime-CH$_3$), 1.7–2.0 (m, 4H, CH$_2$), 0.28 (s, 9H, Si(CH$_3$)$_3$); IR (mull) 3152, 1639 (w), 1246, 1232, 913, 840, 761 cm$^{-1}$; UV (EtOH) $\lambda_{max}$ ($\epsilon$) 237 (8240); MS m/e (relative intensity) 251 (M$^+$, 10), 238 (5), 237 (18), 236 (100), 162 (28) Anal. Calcd for $C_{12}H_{21}N_3OSi$: C, 57.33; H, 8.42; N, 16.71; Found: C, 57.41; H, 8.43; N, 16.56; TLC (SiO$_2$) Rf=0.55, 60% ethyl acetate/hexane.

Example 17

Ethanone 1-(5,6,7,8-tetrahydro-2-methylimidazo[1,2-a]pyridin-3-yl)-,oxime (E-3, Scheme E)

Ethanone, 1-(5,6,7,8-tetrahydro-2-methylimidazo[1,2-a]pyridin-3-yl)- (2.4 g, 13.5 mmole) and hydroxylamine hydrochloride (1.1 g, 16.2 mmole) were refluxed in absolute ethanol (23 mL) and pyridine (11 mL) for 16 hours. The cooled reaction mixture was diluted with 1.0M sodium hydroxide and extracted with methylene chloride (3×50 mL). The organic layers were dried over magnesium sulfate and concentrated to produce a clear oil, which solidified upon standing. The solid was dissolved in refluxing methylene chloride (10 mL) and hexane (10 mL) was added to produce 836.1 mg (32%) of white crystals, containing a 1.7:1 ratio of oxime isomers, after cooling.

$^1$H NMR (CDCl$_3$)δ major isomer: 3.95 (t, 2H, NCH$_2$, J=5 Hz), 2.8–2.9 (m, 2H, 8-CH$_2$), 2.28 (s, 3H, CH$_3$), 2.22 (s, 3H, CH$_3$), 1.8–2.0 (m, 4H, CH$_2$); minor isomer: 3.8–3.9 (m, 2H, NCH$_2$), 2.8–2.9 (m, 2H, 4-CH$_2$), 2.20 (s, 3H, 1H$_3$), 2.14 (s, 3H, CH$_3$), 1.8–2.0 (m, 4H, CH$_2$); IR (mull) 2812, 1620, 1503, 975, 954, 919 cm$^{-1}$; UV (EtOH) $\lambda_{max}$ ($\epsilon$) 261 (8,430): MS m/e (relative intensity) 193 (M$^+$, 54), 177 (11), 176 (100), 149 (11), 148 (22); Anal. Calc'd for $C_{10}H_{15}N_3O$: C, 62.15; H, 7.82; N, 21.74; Found: C, 61.70; H, 7.97; N, 20.71; Exact Mass Calc'd=193.1215; Found=193.1212; TLC (silica) R$_f$ 0.37, 10% methanol/chloroform.

Example 18

1-Propanone, 1-(5,6,7,8-tetrahydro-2-methyl-4H-pyrazolo[1,5-a]azepin-3-yl)-, oxime (A- 4, Scheme A)

Following the procedure described in Example 15 but substituting methyl iodide for diphenyldisulfide yields the title compound.

$^1$H NMR (CDCl$_3$) 8.32 (bs, 1H), 4.19 (m, 2H), 2.74 (m, 2H), 2.60 (q, 2H, J=7 Hz), 2.12 (s, 3H), 1.6–1.9 (m, 6H), 1.03 (t, 3H, J=7 Hz).

Example 19

Ethanone, 1-pyrazolo[1,5-a]pyridin-3-yl

To a solution of Pyridinium, 1-amino-, salt with 2,4,6-trimethylbenzenesulfonic acid (1:1) (20 g, 67.9 mmole) in DMF (136 mL) was added potassium carbonate (10 g) and the solution stirred at room temperature for 30 minutes. 3-butyn-2-one (10 mL, 136 mmole) was added dropwise to the deep blue solution and the resulting orange solution was stirred at room temperature overnight. The reaction mixture was diluted with water (140 mL) and extracted with ether (8×250 mL) and methylene chloride (4×250 mL). The organic layers were dried over magnesium sulfate and concentrated to produce a yellow oil. Several chromatographies and recrystallizations failed to separate the product from unidentifiable impurities.

The crude ketone (5 g, 31 mmole) and hydroxylamine hydrochloride (2.6 g, 37 mmole) were refluxed in absolute ethanol (50 mL) and pyridine (30 mL) for 16 hours. The cooled reaction mixture was diluted with water (250 mL) and extracted with methylene chloride (4×250 mL). The organic layers were dried over magnesium sulfate and concentrated to product a brown solid which was dissolved in refluxing methylene chloride (80 mL) and hexane (80 mL). Cooling produced 1.80 g (33%) of the title compound as brown crystals (m.p. 151°–153° C.).

$^1$H NMR (CDCl$_3$) δ 8.51 (d, 1H, 7-CH, J=7 Hz), 8.1–8.2 (m, 2H, 4-CH, pyrazole-H), 7.2–7.3 (m, 1H, 5-CH), 6.86 (t, 1H, 6-CH, J=7 Hz), 2.36 (s, 3H, CH$_3$); IR (mull) 3252, 1634, 1543, 1535, 1482, 1446, 1274, 1230, 1220, 991,909, 903, 762, 753 cm$^{-1}$; UV (EtOH) $\lambda_{max}$ ($\epsilon$) 227 (17130), 246 sl. sh. (7900), 253 (8490), 260 sh. (6550), 299 sh. (6530), 305 (6820), 327 sh. (4700); MS m/e (relative intensity) 175 (M$^+$, 100), 158 (45), 143 (45), 118 (83), 117 (17); Anal. Calcd for $C_9H_9N_3O$: C, 61.70; H, 5.18; N, 23.99; Found: C, 61.60; H, 5.45; N, 23.69; TLC (SiO$_2$) R$_f$=0.39, 60% ethyl acetate/hexane.

Example 20

Ethanone, 1-[2-methyl-5-(phenylmethyl)pyrazolo[1,5-a]pyridin-3-yl]-, oxime (C-3, Scheme C)

Ethanone, 1-[2-methyl-5-(phenylmethyl)pyrazolo[ 1,5-a]pyridin-3-yl]- (4.46 g, 16.8 mmole) and hydroxylamine hydrochloride (2.0 g, 28.7 mmole) were refluxed in absolute ethanol (27 mL) and pyridine (15 mL) for 6.5 hours. The cooled reaction mixture was diluted with 1.0M sodium hydroxide (200 mL) and extracted with methylene chloride (3×200 mL). The organic layers were dried over magnesium sulfate and concentrated to produce a yellow oil which was dissolved in refluxing methylene chloride (50 mL) and hexane (175 mL). Cooling produced 3.32 g (71%) the title compound as off-white crystals (m.p. 164°–165° C.).

$^1$H NMR (CDCl$_3$) δ8.3–8.6 (bs, 1H, OH), 8.26 (d, 1H, NCH, J=7 Hz), 7.61 (s, 1H, 4-CH), 7.2–7.4 (m, 5H, phenyl-H), 6.53 (dd, 1H, 6-CH, J=7 Hz, 2 Hz), 3.96 (s, 2H, CH$_2$), 2.56 (s, 3H, CH$_3$), 2.35 (s, 3H, CH$_3$); IR (mull) 3227, 3193, 3133, 3084, 3071, 3054, 3028, 3012, 1641. 1539, 1494, 1450, 1426, 1409, 1357, 1245, 1024, 991,928, 914, 794, 760, 732, 703, 609 cm$^{-1}$; UV (EtOH) $\lambda_{max}$ ($\epsilon$) 236 (34650), 255 sh. (10500), 262 sh. (8860), 268 sh. (6790), 277 sh. (7110), 303 (7450), 330 (3730); MS m/e (relative intensity) 280 (20), 279 (100, M$^+$), 262 (34), 222 (89), 195 (29); Anal Calcd for $C_{17}H_{17}N_3O$: C, 73.10; H, 6.13; N, 15.04; Found: C, 73.32; H, 6.07; N, 15.29; TLC (SiO$_2$) R$_f$0.67, 60% ethyl acetate/hexane.

Example 21

Ethanone, 1-(2-methyl-5-phenylpyrazolo[1,5-a]pyridin-3-yl)-, oxime (C-3, Scheme C)

Ethanone, 1-(2-methyl-5-phenylpyrazolo[1,5-a]pyridin-3-yl)-(10 g, 40 mmole) and hydroxylamine hydrochloride (3.5 g, 52 mmole) were refluxed in absolute ethanol (64 mL) and pyridine (35 mL) for 23.5 hours. The cooled reaction mixture was diluted with water (200 mL) and extracted with methylene chloride (3×200 mL). The organic layers were dried over magnesium sulfate and concentrated to produce a yellow solid which was dissolved in refluxing methylene chloride (225 mL) and hexane (150 mL). Cooling produced 6.92 g (65%) of the title compound as yellow crystals (m.p. 190°–192° C.). $^1$H NMR (CDCl$_3$) δ 8.5–8.8 (bs, 1H, OH), 8.43 (d, 1H, NCH, J=7 Hz), 8.00 (s, 1H, 4-CH), 7.64 (d, 2H, phenyl-H, J=7 Hz), 7.3–7.5 (m, 3H, phenyl-H), 7.00 (dd, 1H, 6-CH, J=7 Hz, 2 Hz), 2.61 (s, 3H, CH$_3$), 2.40 (s, 3H, CH$_3$); IR (mull) 3168, 3129, 3066, 3020, 1638, 1537, 1438, 1357, 1251, 993, 915, 755,695, 687 cm$^{-1}$; UV (EtOH) λ$_{max}$ (ε) 254 (35200), 263 sh. (29050), 324 (6170), 338 (6570); MS m/e (relative intensity) 265 (100, M$^+$), 248 (28), 233 (21), 208 (81), 181 (35); Anal. Calcd for C$_{16}$H$_{15}$N$_3$O: C, 72.43; H, 5.70; N, 15.84; Found: C, 72.24; H, 5.82; N, 15.92; TLC (SiO$_2$) R$_f$=0.33, 10% methanol/chloroform.

Example 22
Ethanone, 1-(6-chloro-2-methylimidazo[1,2-a]pyridin-3-yl)-, oxime (D-3, Scheme D)

Ethanone, 1-(6-chloro-2-methylimidazo-[1,2-a]pyridin-3-yl)- (4.0 g, 19 mmole) and hydroxylamine hydrochloride (2.3 g, 33 mmole) were refluxed in absolute ethanol (38 mL) and pyridine (21 mL) for 16 hours. The cooled reaction mixture was diluted with water (150 mL) and the resulting solid was collected by filtration. The filtrate was extracted with methylene chloride (3×125 mL) and the organic layers were dried over magnesium sulfate and concentrated to produce a brown solid. The solids were combined and dissolved in refluxing 95% ethanol (185 mL) and water (10 mL) to produce 2.87 g (68%) of the title compound as white crystals upon cooling (m.p. 235°–255° C.).

$^1$H NMR (CDCl$_3$) δ 9.24 (s, 1H, 5-H), 7.60 (d, 1H, 8-CH, J=9 Hz), 7.37 (dd, 1H, 7-CH, J=10 Hz, 2 Hz), 2.53 (s, 3H, CH$_3$), 2.30 (s, 3H, CH$_3$); IR (mull) 3151, 3136, 3109, 3079, 3072, 3021, 2800, 2787, 2768, 2705, 2640, 2615, 1615, 1523, 1499, 1450, 1418, 1403, 1366, 1326, 1287, 1060, 1025, 957, 952, 928, 802 cm$^{-1}$; UV (EtOH) λ$_{max}$ (ε) 212 (24400), 223 sh. (19280), 248 sh. (15500), 255 (20610), 264 (21630), 304 (6200), 311 (6100), 336 sh. (2940); MS m/e (relative intensity) 225 (32), 223 (100, M$^+$), 206 (93), 166 (88), 112 (39); Anal. Calcd for C$_{10}$H$_{10}$N$_3$OCl: C, 53.70; H, 4.51; N, 18.79; Cl, 15.85; Found: C, 53.69; H, 4.41; N, 18.68; Cl, 15.93; TLC (SiO$_2$) R$_f$=0.40, 10% methanol/chloroform.

Example 23
Ethanone, 1-(7,8,9,10-tetrahydro-2-methylimidazo[2,1-a]isoquinolin-3-yl)-, oxime (D-3, Scheme D)

Ethanone, 1-(7,8,9,10-tetrahydro-2-methylimidazo[2,1-a]isoquinolin-3-yl)- (6.0 g, 26.2 mmole) and hydroxylamine hydrochloride (2.6 g, 36.7 mmole) were refluxed in absolute ethanol (41 mL) and pyridine (22 mL) for 16 hours. The cooled reaction mixture was diluted with water (300 mL) and the resulting off-white solid was collected by filtration. The filtrate was extracted with methylene chloride (3×500 mL) and the organic layers were dried over magnesium sulfate and concentrated to produce a white solid. The solids were combined and dissolved in 95% ethanol (350 mL) and water (100 mL) was added to produce 3.28 g (51%) of the title compound as light pink crystals upon cooling (m.p. 266°–267° C.).

$^1$H NMR (DMSO) δ 8.73 (d, 1H, 5-H, J=7 Hz), 6.67 (d, 1H, 6-H, J=7 Hz), 2.8–3.0 (m, 2H), 2.6–2.8 (m, 2H), 2.47 (s, 3H, CH$_3$), 2.26 (s, 3H, CH$_3$), 1.7–1.9 (m, 4H, 8-, 9-CH$_2$); IR (mull) 3153, 3119, 3048, 3030, 2817, 2798, 2774, 2707, 1636, 1616, 1497, 1451, 1431, 1414, 968, 922, 909, 788 cm$^{-1}$; UV (EtOH) λ$_{max}$ (ε) 211 (19200), 225 (19400), 241 sh. (18900), 247 (20550), 255 (19020), 301(10380); MS m/e (relative intensity) 244 (17), 243 (M$^+$, 100), 226 (88), 186 (92), 185 (23); Anal. C C$_{14}$H$_{17}$N$_3$O: C, 69.11; H, 7.04; N, 17.27; Found: C, 69.29; H, 6.91; N, 17.48; TLC (SiO$_2$) R$_f$=0.54, 10% methanol/chloroform.

Example 24
Ethanone, 1-[2-methyl:8-(phenylmethoxy)imidazo[1,2a]pyridin-3-yl]-, oxime (D-3, Scheme D)

Ethanone, 1-[2-methyl-8-(phenylmethoxy)imidazo[1,2-a]pyridin-3-yl]- (5.67 g, 20.2 mmole) and hydroxylamine hydrochloride (2.0 g, 28.3 mmole) were refluxed in absolute ethanol (32 mL) and pyridine (17 mL) for 20 hours. The cooled reaction mixture was diluted with water (100 mL) and extracted with methylene chloride (3×100 mL). The organic layers were dried over magnesium sulfate and concentrated to produce 4.67 g of a brown oil, which was dissolved in refluxing methylene chloride (350 mL) and hexane (150 mL) to produce 3.58 g (60%) of the title compound as brown crystals upon cooling. An analytical sample was obtained by recrystallization from 95% ethanol and water (m.p. 207°–209° C.).

$^1$H NMR (CDCl$_3$) δ 8.53 (d, 1H, 5-H, J=7 Hz), 7.4–7.6 (m, 2H, phenyl-H), 7.2–7.4 (m, 3H, phenyl-H), 6.62 (t, 1H, 6-H, J=8 Hz), 6.51 (d, 2H, 7-H, J=8 Hz), 5.33 (s, 2H, CH$_2$), 2.64 (s, 3H, CH$_3$), 2.38 (s, 3H, CH$_3$); IR (mull) 2811, 1556, 1507, 1433, 1412, 1364, 1292, 1275, 1033, 1028, 943, 747, 734, 695, 604 cm$^{-1}$; UV (EtOH) λ$_{max}$ (ε) 233 (21820), 242 sl. sh. (23600), 248 (25800), 255 (22860), 300 (8400); MS m/e (relative intensity) 296 (14), 295 (M$^+$, 68), 218 (28), 189 (24), 91 (100); Anal. Calcd for C$_{17}$H$_{17}$N$_3$O$_2$: C, 69.14; H, 5.80; N, 14.23; Found: C, 69.18; H, 6.00; N, 14.20; TLC (SiO$_2$) R$_f$=0.48, 10% methanol/chloroform.

Example 25
Ethanone, 1-(2-methylimidazo[2,1-a]isoquinolin-3-yl)-, oxime (D-3, Scheme D)

Ethanone, 1-(2-methylimidazo[2,1-a]isoquinolin-3-yl)- (6.3 g, 28 mmole) and hydroxylamine hydrochloride (2.9 g, 42 mmole) were refluxed in absolute ethanol (41 mL) and pyridine (22 mL) for 18 hours. The cooled reaction mixture was diluted with water (500 mL) and the resulting orange solid was collected by filtration. The filtrate was extracted with methylene chloride (2×500 mL). The organic layers were dried over magnesium sulfate and concentrated to produce an orange solid. The solids were combined and dissolved in refluxing 95% ethanol (1.5 L) and water (1 L) to produce 4.84 g (72%) of the title compound as light pink crystals upon cooling (m.p. 283°–285° C. dec.).

$^1$H NMR (DMSO) δ 11.44 (s, 1H, OH), 8.67 (d, 1H, 5-H, J=7 Hz), 8.4–8.5 (m, 1H), 7.7–7.9 (m, 3H), 7.28 (d, 1H, J=8 Hz), 2.53 (s, 3H, CH$_3$), 2.31 (s, 3H, CH$_3$); IR (mull) 3131, 3047, 3010, 2812, 2791, 2765, 2687, 2642, 1516, 1408, 1366, 1016, 935, 929, 796, 698 cm$^{-1}$; UV (EtOH) λ$_{max}$ (ε) 213 (17700), 241 sl. sh. (16680), 261 (39920), 307 (10200); MS m/e (relative intensity) 239 (M$^+$, 100), 222 (86), 182 (78), 181 (22), 128 (41); Anal. Calcd for C$_{14}$H$_{13}$N$_3$O: C, 70.28; H, 5.48; N, 17.56; Found: C, 70.14; H, 5.75; N, 17.18; TLC (SiO$_2$) R$_f$=0.54, 10% methanol/chloroform.

Example 26
Ethanone, 1-(8-acetamido-2-methylimidazo[1,2-a]pyridin-3-yl)-, oxime (D-3, Scheme D)

Acetamide, N-(3-acetyl-2-methylimidazo[1,2-a]pyridin-8-yl)- (4.6 g, 19.9 mmole), hydroxylamine hydrochloride (1.8 g, 25.9 mmole) and sodium acetate (2.0 g) were refluxed in absolute ethanol (40 mL) for 5.5 hours. The cooled reaction mixture was diluted with water (250 mL) and the resulting solid was collected by filtration. The filtrate was extracted with methylene chloride (2×250 mL) and the organic layers were dried over magnesium sulfate and concentrated to produce a yellow oil. The oil and the solid were combined and dissolved in refluxing 95% ethanol (325 mL) and water (160 mL) to produce 2.10 g (43%) of the title compound as off-white crystals upon cooling (280°–281° C., dec.).

$^1$H NMR (DMSO) δ 11.37 (s, 1H, OH), 9.94 (s, 1H, NH), 8.63 (d, 1H, 5-H, J=7 Hz), 7.98 (d, 1H, 7-H, J=8 Hz), 6.90 (t, 1H, 6-H, J=7 Hz), 2.53 (s, 3H, $CH_3$), 2.28 (s, 3H, $CH_3$), 2.21 (s, 3H, $CH_3$); IR (mull) 3399, 3381, 1703, 1694, 1641, 1622, 1559, 1535, 1451, 1427, 1410, 1367, 1292, 1280, 1246, 1017, 924, 740 cm$^{-1}$; UV (EtOH) $\lambda_{max}$ (ε) 209 (18520), 251 sl. sh. (25650), 258 (34780), 267 (37450), 304 (7080); MS m/e (relative intensity) 246 (M$^+$, 100), 231 (46), 204 (55), 187 (79), 147 (49); Anal. Calcd for $C_{12}H_{14}N_4O_2$: C, 58.53; H, 5.73; N, 22.75; Found: C, 58.44; H, 5.87; N, 22.55; TLC (SiO$_2$) R$_f$=0.44, 10% methanol/chloroform.

Example 27

Methanone, (2-methylimidazo[1,2-a]pyridin-3-yl)phenyl-, oxime (D-3, Scheme D)

Methanone, (2-methylimidazo[1,2-a]pyridin-3-yl)phenyl- (9.0 g, 38 mmole) and hydroxylamine hydrochloride (4.0 g, 57 mmole) were refluxed in absolute ethanol (76 mL) and pyridine (38 mL) for 24 hours. The cooled reaction mixture was diluted with water (500 mL) and the resulting solid was collected by filtration. The filtrate was extracted with methylene chloride (4×500 mL) and the organic layers were dried over magnesium sulfate and concentrated to produce a yellow solid. The solids were combined and dissolved in refluxing 95% ethanol (100 mL) and water (75 mL) to produce 6.86 g (72%) of white crystals upon cooling. This material contained a 2.5:1 ratio of oxime isomers (m.p. 217°–220° C.) with the title compound being the major isomer.

$^1$H NMR (DMSO)δ Major Isomer: 12.08 (s, 1H, OH), 7.73 (d, 1H, 5-H, J=7 Hz), 7.59 (d, 1H, 8-CH, J=9 Hz), 7.4–7.5 (m, 5H, phenyl-H), 7.32 (td, 1H, 7-H, J=7 Hz), 6.91 (td, 1H, 6-H, J=7 Hz, 1 Hz), 2.05 (s, 3H, imidazole-$CH_3$); IR (mull) 2779, 2663, 2651, 2642, 2628, 2592, 2571, 1504, 1493, 1438, 1409, 1243, 1035, 1027, 1002, 963, 952, 764, 753, 741, 693 cm$^{-1}$; UV (EtOH) $\lambda_{max}$ (ε) 208 (28650), 235 (27750), 258 sh. (14960), 273 sh. (9890) 308 (7000); MS m/e (relative intensity) 251 (M$^+$, 59), 234 (36), 219 (13), 132 (100), 78 (31); Anal. Calcd for $C_{15}H_{13}N_3O$: C, 71.70; H, 5.21; N, 16.72; Found: C, 71.80; H, 5.42; N, 16.41; TLC (SiO$_2$) R$_f$=0.55, ethyl acetate Example 28

Ethanone, 1-(2-phenylimidazo[1,2-]pyridin-3-yl)-, oxime (D-3, Scheme D)

Ethanone, 1-(2-phenylimidazo[1,2-a]pyridin-3-yl)- (2.95 g, 12.5 mmole) and hydroxylamine hydrochloride (1.3 g, 18.7 mmole) were refluxed in absolute ethanol (25 mL) and pyridine (8.5 mL) for 24 hours. The cooled reaction mixture was diluted with water (200 mL) and extracted with methylene chloride (4×200 mL). The organic layers were dried over magnesium sulfate and concentrated to produce a white solid which was dissolved in refluxing 95% ethanol (100 mL) and water (125 mL) to produce 2.54 g (81%) of white crystals upon cooling. This material contained a 1.9:1 ratio of oxime isomers (m.p. 209°–210° C.) with the title compound being the major isomer.

$^1$H NMR (DMSO)δ Major Isomer: 11.71 (s, 1H, OH), 8.71 (d, 1H, 5-H, J=7 Hz), 7.6–7.8 (m, 3H, phenyl-H, 8-H), 7.3–7.6 (m, 4H, phenyl-H, 7-H), 7.03 (td, 1H, 6-H, J=7 Hz, 1 Hz), 2.09 (s, 3H, $CH_3$); IR (mull) 3111, 3076, 3054, 3029, 2806, 2755, 1503, 1445, 1397, 1362, 1032, 1019, 1008, 920, 776, 756, 740, 697 cm$^{-1}$; UV (EtOH) $\lambda_{max}$ (ε) 208 (29300), 246 (35190), 309 (7480), 321 (6460); MS m/e (relative intensity) 251 (M$^+$, 100), 234 (97), 219 (61), 194 (81), 78 (49); Anal. Calcd for $C_{15}H_{13}N_3O$: C, 71.70; H, 5.21; N, 16.72; Found: C, 71.71; H, 5.25; N, 16.87; TLC (SiO$_2$) R$_f$=0.85, ethyl acetate.

Example 29

Ethanone, 1-(6-bromo-2-methylimidazo[1,2-a]pyridin-3-yl)-, oxime (D-3, Scheme D)

Ethanone, 1-(6-bromo-2-methylimidazo[1,2-a]pyridin-3-yl)- (6.5 g, 25.7 mmole) and hydroxylamine hydrochloride (2.8 g, 38.5 mmole) were refluxed in absolute ethanol (41 mL) and pyridine (21 mL) for 20 hours. The cooled reaction mixture was diluted with water (500 mL) and the resulting solid collected by filtration. The filtrate was extracted with methylene chloride (3×500 mL) and the organic layers were dried over magnesium sulfate and concentrated to produce a brown oil. The oil and the solid were combined and purified by flash chromatography (5% methanol/chloroform, 250 g silica) to produce 3.68 g (53%) of brown crystals. This material was dissolved in refluxing 95% ethanol (175 mL) and water (100 mL) to produce 2.26 g (33%) of the title compound as brown crystals upon cooling (m.p. 241°–243° C.).

$^1$H NMR (DMSO) δ 11.45 (s, 1H, OH), 9.32 (s, 1H, 5-H), 7.55 (d, 1H, 8-H, J=9 Hz), 7.4–7.5 (m, 1H, 7-H), 2.53 (s, 3H, $CH_3$), 2.30 (s, 3H, $CH_3$); IR (mull) 3136, 3107, 3066, 3044, 3018, 2810, 2794, 1612, 1518, 1498, 1451, 1419, 1397, 1326, 1288, 1049, 1028, 945, 923, 855, 796, 695 cm$^{-1}$; UV (EtOH) $\lambda_{max}$ (ε) 213 (25400), 249 sh. (15010), 257 (19520), 266 (20810), 306 (6170), 335 (3200); MS m/e (relative intensity) 269 (99), 268 (M$^+$, 13), 267 (100), 250 (82), 212 (87), 210 (89), 252 (80); Anal. Calcd for $C_{10}H_{10}N_3OBr$: C, 44.78; H, 3.76; N, 15.67; Found: C, 45.21; H, 3.69; N, 15.60; TLC (SiO$_2$) R$_f$=0.84, 10% methanol/chloroform.

Example 30

Ethanone, 1-(2,5-dimethylimidazo[1,2-a]pyridin-3-yl)-, oxime (D-3, Scheme D)

Ethanone, 1-(2,5-dimethylimidazo[1,2-a]pyridin-3-yl)- (100 mg, 0.53 mmole) and hydroxylamine hydrochloride (111 mg, 1.59 mmole) were refluxed in absolute ethanol (6 mL) for 7 days. The cooled reaction mixture was diluted with brine (15 mL) and extracted with ethyl acetate (3×30 mL) and methylene chloride (3×30 mL). The organic layers were dried over magnesium sulfate and concentrated to produce 100.6 mg (93%) of white crystals, pure by NMR. An analytical sample could be obtained by recrystallization from refluxing ethyl acetate and petroleum ether (1:1 ratio) to produce a 2.8:1 milo of oxime isomers as white crystals (m.p. 188°–190° C. dec.) with the title compound being the major isomer.

$^1$H NMR(CDCl$_3$)δ Major Isomer: 11.6–11.8 (bs, 1H, OH), 7.50 (d, 1H, 8-H, J=9 Hz), 7.0–7.2 (m, 1H, 7-H), 6.5–6.6 (m, 1H, 6-H), 2.61 (s, 3H, $CH_3$), 2.46 (s, 3H, $CH_3$), 2.30 (s, 3H, $CH_3$); IR (mull) 2802, 2795, 2762, 2641, 1516, 1441, 1412, 1360, 1322, 1153, 1013, 943, 777, 737 cm$^{-1}$; UV (EtOH) $\lambda_{max}$ (ε) 222 sh. (23320), 226 (24500), 232 (22500), 247 sh. (7380), 290 (6140); MS m/e (relative intensity) 203 (M$^+$, 46), 186 (56), 171 (58), 146 (100), 92 (54); Anal. Calcd for $C_{11}H_{13}N_3O$: C, 65.00; H, 6.45; N, 20.67; Found: C, 64.82; H, 6.57; N, 20.67; TLC (SiO$_2$) R$_f$=0.21, ethyl acetate.

Example 31

Ethanone, 1-(8-hydroxy-2-methylimidazo[1,2-a]pyridin-3-yl)-, oxime

Ethanone, 1-[2-methyl-8-(phenylmethoxy)imidazo[1,2-a]pyridin-3-yl]-, oxime (20.13 g, 68.16 mmole), cyclohexene (270 mL) and 10% Pd/C (6.0 g) were refluxed in absolute ethanol (974 mL) for 2 hours. The Pd/C was removed by filtration through celite and the filtrate concentrated to produce a green solid which was dissolved in refluxing ethanol (1 L) and water (2000 mL) to produce 9.42 g (68%) of the title compound as brown crystals upon cooling (m.p. 254°–256° C. dec.).

$^1$H NMR (DMSO)δ 8.45 (dd, 1H, 5-H, J=1 Hz, 7 Hz), 6.79 (t, 1H, 6-H, J=7 Hz), 6.58 (dd, 1H, 7-H, J=1 Hz, 7 Hz), 2.52 (s, 3H, $CH_3$), 2.30 (s, 3H, $CH_3$); IR (mull) 3075, 3053, 2786, 2755, 2660, 2604, 2573, 2541, 1565, 1497, 1448, 1288, 1268, 1228, 1069, 1034, 946, 835, 749 cm$^{-1}$; UV (EtOH) $\lambda_{max}$ (ε) 229 (18120), 242 sl. sh. (19360), 248 (20870), 255 (18570), 304 (8930); MS m/e (relative intensity) 205 (M$^+$, 80),188 (32),148 (27), 80 (26) 38 (100); Anal. Calcd for $C_{10}H_{11}N_3O_2$: C, 58.53; H, 5.40; N, 20.48; Found: C, 58.60; H, 5.44; N, 20.51; TLC ($SiO_2$) $R_f$=0.24, ethyl acetate.

Example 32

Ethanone, 1-(2-methylimidazo[1,2-a]pyridin-3-yl)-acetyl hydrazone 1-(2-methylimidazo[1,2-a]pyridin-3-yl)- Ethanone, (32 g, 0.183 mole)and acetic hydrazide (68 g, 0.918 mole) were refluxed in THF (120 mL and acetic acid (1.1 mL) for 10 days. The cooled reaction mixture was filtered and the filtrate diluted with methylene chloride (500 mL) and washed with water (3×500 mL). The aqueous phase was made basic with solid potassium hydroxide, the solution was filtered and the filtrate extracted with chloroform (3×500 mL). The organic phase was dried over magnesium sulfate and concentrated under reduced pressure to produce a yellow solid which was dissolved in refluxing methylene chloride (350 mL) and hexane (50 mL) and cooled at 0° C. for 1.5 hours to produce a white solid upon cooling. Subsequent recrystallizations produced a total of 7.50 g (17%) of white crystals as a mixture of isomers (m.p. 196°–198° C.).

$^1$H NMR (CDCl$_3$)δ 9.18 (dt, 1H, S-H, J=7 Hz, 1 Hz), 8.8–8.9 Cos, 1H, NH), 7.64 (dt, 1H, 8-H, J=9 Hz, 2 Hz), 7.3–7.4 (m, 1H, 7-H), 6.95 (t, 1H, 6-H, J=7 Hz), 2.72 (s, 3H, $CH_3$), 2.45 (s, 3H, $CH_3$), 2.44 (s, 3H, $CH_3$); IR (mull) 3033, 1676, 1662, 1446, 1403, 1389, 1366, 1353, 1286, 1274, 756, 629, 611 cm$^{-1}$; UV (EtOH) $\lambda_{max}$ (ε) 218 (25070), 253 sl. sh. (14200), 261 (19700), 270 (22600), 321 ( 13300); MS m/e (relative intensity) 230 (M$^+$, 100), 159 (43), 158 (27), 157 (61), 132 (78); Anal. Calcd for $C_{12}H_{14}N_4O$: C, 62.59; H, 6.13; N, 24.33; Found: C, 62.40; H, 6.21; N, 24.33; TLC ($SiO_2$) $R_f$=0.64, 10% methanol/chloroform.

The compounds of this invention are useful for the treatment of atherosclerosis and hypochlosterolemia. These utilities of the compounds are shown by the following test.

I. Anti-Atherosclerotic Activity

Male Japanese quail, four to six weeks of age, were randomly distributed into groups of 10 quail each. The birds were housed individually in 10-cage units and fed a commercial chow (Purina Game Bird Layena, Ralston Purina Co., St. Louis, Mo.) or the commercial chow supplemented with 0.5% cholesterol and 1% peanut oil. Test compounds were dissolved or suspended in 95% ethanol and mixed into the diets. The drug-containing diets were fed to the animals for either 7 days (chow-fed) or 14 days (cholesterol-fed). The dosage of drug administered in each case was 50 mg/kg.

At the end of the treatment period, each bird was bled from the right jugular vein and serum samples were obtained after low speed centrifugation. β- and α-lipoproteins (VLDL+LDL and HDL, respectively) were isolated from individual serum samples by precipitation using PEG-8000. Cholesterol concentrations in the α- and β-lipoprotein fractions were measured using a Demand autoanalyzer and Demand enzymatic reagents. All data were analyzed using a one-way classification design after transforming the data to logarithms to achieve more homogeneous within-group variances.

TABLE 1

Serum Cholesterol Data (LDL + VLDL) for Selected Compounds of the Invention. Data from Chow-Fed Quail.

| Compound Number | LDL + VLDL Cholesterol T/C |
| --- | --- |
| 1 | 0.56 |
| 2 | 0.76 |
| 3 | 0.82 |
| 4 | 0.75 |
| 5 | 0.82 |
| 6 | 0.52 |
| 7 | 0.85 |
| 8 | 0.71 |
| 9 | 0.56 |
| 10 | 0.82 |
| 11 | 0.78 |
| 12 | 0.81 |
| 13 | 0.77 |
| 14 | 0.59 |
| 15 | 0.74 |
| 16 | 0.41 |
| 17 | 0.78 |
| 18 | 0.70 |
| 19 | 0.61 |
| 20 | 0.62 |

TABLE 2

Serum Cholesterol Data (LDL + VLDL) for Selected Compounds of the Invention. Data from Cholesterol-Fed Quail.

| Compound Number | LDL + VLDL Cholesterol T/C |
| --- | --- |
| 1 | 0.56 |
| 6 | 0.34 |
| 21 | 0.64 |
| 22 | 0.81 |
| 16 | 0.72 |
| 18 | 0.52 |
| 23 | 0.49 |
| 20 | 0.62 |
| 24 | 0.84 |
| 25 | 0.47 |
| 26 | 0.43 |
| 27 | 0.75 |
| 28 | 0.34 |
| 29 | 0.51 |
| 30 | 0.81 |
| 31 | 0.59 |
| 32 | 0.72 |

Tables 1 and 2 show results for those compounds which have been tested in chow-fed quail or cholesterol-fed quail, respectively, for their ability to reduce serum cholesterol levels. A ratio of drug treated/control (T/C) serum cholesterol levels of 0.85 or less was considered active.

The compound Ethanone, 1-(3-methylimidazo[1,5-a]pyridin-1-yl)-, oxime and its use in the treatment of atherosclerosis and hypercholesterolemia is contemplated as the best mode of practicing this invention.

| KEY TO NAME OF COMPOUND: | |
| --- | --- |
| Number | Name |
| 1. | Ethanone, 1-(5,6,7,8-tetrahydro-2-methyl-4H-pyrazolo-[1,5-a]azepine-3-yl)-, oxime |
| 2. | Ethanone, 1-(5,6,7,8-tetrahydro-2-methyl-4H-pyrazolo[1,5-a]azepin-3-yl)-, O-acetyloxime |

KEY TO NAME OF COMPOUND:

| Number | Name |
|---|---|
| 3. | Ethanone, 1-(5,6,7,8-tetrahydro-2-methyl-4H-pyrazolo[1,5-a]azepin-3-yl)-,O-(2-hydroxyethyl)oxime |
| 4. | Ethanone, 2-(phenylthio)-1-(5,6,7,8-tetrahydro-2-methyl-4H-pyrazolo[1,5-a]azepin-3-yl)-, oxime |
| 5. | 1-Propanone, 1-(5,6,7,8-tetrahydro-2-methyl-4H-pyrazolo[1,5-a]azepin-3-yl)-, oxime |
| 6. | Ethanone, 1-(4,5,6,7-tetrahydro-2-methylpyrazolo[1,5-a]pyridin-3-yl)-, oxime |
| 7. | Ethanone, 1-(4,5,6,7-tetrahydro-2-phenylpyrazolo[1,5-a]pyridin-3-yl)-, oxime |
| 8. | Ethanone, 1-(4,5,6,7-tetrahydro-2-propylpyrazolo[1,5-a]pyridin-3-yl)-, oxime) |
| 9. | Ethanone, 1-(2-methylpyrazolo[1,5-a]pyridin-3-yl)-, oxime |
| 10. | Ethanone, 1-[2-(2-furanyl)-4,5,6,7-tetrahydropyrazolo[1,5-a]pyridin-3-yl]-, oxime |
| 11. | Ethanone, 1-[2-(3,4-dimethoxyphenyl)-4,5,6,7-tetrahydropyrazolo[1,5a]pyridin-3-yl]-, oxime |
| 12. | Ethanone, 1-[4,5,6,7-tetrahydro-2-(phenoxymethyl)pyrazolo[1,5-a]pyridin-3-yl]-, oxime |
| 13. | Ethanone, 1-(4,5,6,7-tetrahydro-2-trimethylsilylpyrazolo[1,5-a]pyridin-3-yl)-, oxime |
| 14. | Ethanone, 1-pyrazolo[1,5-a]pyridin-3-yl, oxime |
| 15. | Ethanone, 1-(5,6-dihydro-2-methyl-4H-pyrrolo[1,2-b]pyrazol-3-yl)-, oxime |
| 16. | Ethanone, 1-(3-methylimidazo[1,5-a]pyridin-1-yl)-, oxime |
| 17. | Ethanone, 1-(5,6,7,8-tetrahydro-3-methylimidazo[1,5-a]pyridin-1-yl)-, oxime, monohydrochloride |
| 18. | Ethanone, 1-(2-methylimidazo[1,2-a]pyridin-3-yl)-, oxime |
| 19. | Ethanone, 1-(5,6,7,8-tetrahydro-2-methylimidazo[1,2-a]pyridin-3-yl)-, oxime |
| 20. | Ethanone, 1-(7,8,9,10-tetrahydro-2-methylimidazo[2,1-a]isoquinolin-3-yl)-, oxime |
| 21. | Ethanone, 1-[2-methyl-5-(phenylmethyl)pyrazolo[1,5-a]pyridin-3-yl]-, oxime |
| 22. | Ethanone, 1-(2-methyl-5-phenylpyrazolo[1,5-a]pyridin-3-yl)-, oxime |
| 23. | Ethanone, 1-(6-chloro-2-methylimidazo[1,2-a]pyridin-3-yl)-, oxime |
| 24. | Ethanone, 1-[2-methyl-8-(phenylmethoxy)imidazo[1,2-a]pyridin-3-yl]-, oxime |
| 25. | Ethanone, 1-(2-methylimidazo[2,1-a]isoquinolin-3-yl-, oxime |
| 26. | Acetamide, N-[3-[1-(hydroxyimino)ethyl]2-2methyl imidazo[1,2-a]pyridin-8-yl]- |
| 27. | Methanone, (2-methylimidazo[1,2-a]pyridin-3-yl) phenyl-, oxime |
| 28. | Ethanone, 1-(2-phenylimidazo[1,2-a]pyridin-3-yl)-, oxime |
| 29. | Ethanone, 1-(6-bromo-2-methylimidazo[1,2-a]pyridin-3-yl, oxime |
| 30. | Ethanone, 1-(2,5-dimethylimidazo[1,2-a]pyridin-3-yl)-, oxime |
| 31. | Ethanone, 1-(8-hydroxy-2-methylimidazo[1,2-a]pyridin-3-yl)-, oxime |
| 32. | Ethanone, 1-(2-methylimidazo[1,2-a]pyridin-3-yl)-, acetyl hydrazone |

We claim:

1. A compound having the structural formula Ia

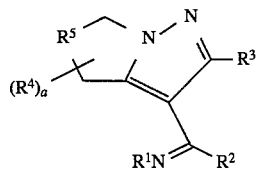

wherein $R^1$ is
(a) hydroxy,
(b) $OC(O)C_1-C_5$ alkyl,
(c) $O-C_1-C_5$ alkyl $-OH$, and
(d) $NHC(O)C_1-C_5$ alkyl; or
wherein $R^2$ is
(a) straight chain $C_1-C_8$ alkyl, or
(b) phenyl-X,
(c) $C_1-C_5$ alkyl-$R^6$-phenyl-X;
wherein $R^3$ is
(a) hydrogen,
(b) $C_1-C_8$ alkyl,
(c) furanyl,
(d) $C_1-C_5$ alkyl-$R^6$-phenyl-X,
(e) phenyl-X, or
(f) Si $(C_1-C_5$ alkyl$)_3$;
wherein $R^4$ is
(a) phenyl-X,
(b) $C_1-C_5$ alkyl-phenyl-X,
(c) halogen,
(d) $C_1-C_8$ alkyl,
(e) OH,
(f) $OC_1-C_5$ alkyl-phenyl-X,
(g) $NHC(O)C_1-C_5$ alkyl, or
(h) $OC(O)C_1-C_5$ alkyl;
(i) hydrogen, or
(j) $R^4$ together with two adjacent carbons on the ring to which it is attached form a cyclopentyl, hexyl, heptyl or octyl ring or an aromatic form thereof;
wherein $R^5$ is $-(CH_2)_c-$ and $c$ is 1;
wherein $R^6$ is,
(a) O—,
(b) S—, or
(c) $CH_2-$;
a is 1–4;
wherein phenyl-X is phenyl substituted by 1 to 3 same or different substituent selected from the group
(a) H,
(b) halogen,
(c) OH,
(d) $OC_1-C_5$ alkyl,
(e) $SC_1-C_5$ alkyl,
(f) $NH_2$,
(g) $N(C_1-C_5$ alkyl$)_2$,
(h) $NHC(O)C_1-C_5$ alkyl,
(i) $OC(O)C_1-C_5$ alkyl,
(j) $CF_3$,
(k) CN, or
(l) $CO_2C_1-C_5$ alkyl;
or pharmaceutically acceptable acid addition salts thereof; with proviso that where $R^1$ is hydroxy or $-NHC(O)C_1-C_5$ alkyl, $R^2$ is not $-C_1-C_6$ alkyl, $R^3$ is not $-C_1-C_6$ alkyl or phenyl-X and $R^4$ is not halogen.

2. A compound according to claim 1 which is
Ethanone, 1-(5,6-dihydro-2-methyl-4H-pyrrolo[1,2-b]pyrazol-3-yl)- , oxime.

3. A compound of claim 1 wherein $R^1$ is hydroxy; $R^2$ is straight chain $C_1-C_8$ alkyl; $R^3$ is straight chain $C_1-C_8$ alkyl; and $R^4$ is hydrogen.

4. A method for treating atherosclerosis or hypercholesterolemia by administering a therapeutically effective amount of a compound having the formula

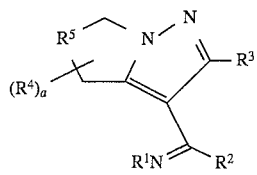

wherein $R^1$ is
(a) hydroxy,
(b) $OC(O)C_1$-$C_5$ alkyl,
(c) O—$C_1$-$C_5$ alkyl —OH, and
(d) $NHC(O)C_1$-$C_5$ alkyl; or
wherein $R^2$ is
(a) straight chain $C_1$-$C_8$ alkyl, or
(b) phenyl-X,
(c) $C_1$-$C_5$ alkyl-$R^6$-phenyl-X;
wherein $R^3$ is
(a) hydrogen,
(b) $C_1$-$C_8$ alkyl,
(c) furanyl,
(d) $C_1$-$C_5$ alkyl-$R^6$-phenyl-X,
(e) phenyl-X, or
(f) Si $(C_1$-$C_5$ alkyl$)_3$;
wherein $R^4$ is
(a) phenyl-X,
(b) $C_1$-$C_5$ alkyl-phenyl-X,
(c) halogen,
(d) $C_1$-$C_8$ alkyl,
(e) OH,
(f) $OC_1$-$C_5$ alkyl-phenyl-X,
(g) $NHC(O)C_1$-$C_5$ alkyl, or
(h) $OC(O)C_1$-$C_5$ alkyl;
(i) hydrogen, or
(j) $R^4$ together with two adjacent carbons on the ring to which it is attached form a cyclopentyl, hexyl, heptyl or octyl ring or an aromatic form thereof;
wherein $R^5$ is —$(CH_2)_c$— and $c$ is 1;
wherein $R^6$ is,
(a) O—,
(b) S—, or
(c) $CH_2$—;
a is 1–4;
wherein phenyl-X is phenyl substituted by 1 to 3 same or different substituent selected from the group
(a) H,
(b) halogen,
(c) OH,
(d) $OC_1$-$C_5$ alkyl,
(e) $SC_1$-$C_5$ alkyl,
(f) $NH_2$,
(g) $N(C_1$-$C_5$ alkyl$)_2$,
(h) $NHC(O)C_1$-$C_5$ alkyl,
(i) $OC(O)C_1$-$C_5$ alkyl,
(j) $CF_3$,
(k) CN, or
(l) $CO_2$ $C_1$-$C_5$ alkyl;
or pharmaceutically acceptable acid addition salts thereof; with proviso that where $R^1$ is hydroxy or —$NHC(O)C_1$-$C_5$ alkyl, $R^2$ is not —$C_1$-$C_6$ alkyl, $R^3$ is not —$C_1$-$C_6$ alkyl or phenyl-X and $R^4$ is not halogen.

\* \* \* \* \*